United States Patent [19]
Ota et al.

[11] Patent Number: 5,621,324
[45] Date of Patent: Apr. 15, 1997

[54] MAGNETIC FIELD GENERATOR FOR MRI

[75] Inventors: Kimiharu Ota; Masaaki Aoki, both of Amagasaki; Hiroyuki Takeuchi, Kashiwa; Yasuhiro Marukawa, Kawanishi; Hirotaka Takeshima, Ryugasaki; Chikako Nakamura, Matudo, all of Japan

[73] Assignee: Sumitomo Special Metals Company Limited, Osaka, Japan

[21] Appl. No.: 146,191

[22] PCT Filed: Mar. 17, 1993

[86] PCT No.: PCT/JP93/00320

§ 371 Date: Jan. 18, 1994

§ 102(e) Date: Jan. 18, 1994

[87] PCT Pub. No.: WO93/18707

PCT Pub. Date: Sep. 30, 1993

[30] Foreign Application Priority Data

| Mar. 18, 1992 | [JP] | Japan | 4-93687 |
| Apr. 10, 1992 | [JP] | Japan | 4-117932 |
| May 15, 1992 | [JP] | Japan | 4-148812 |
| Oct. 29, 1992 | [JP] | Japan | 4-316535 |
| Feb. 25, 1993 | [JP] | Japan | 5-63397 |
| Feb. 25, 1993 | [JP] | Japan | 5-63398 |

[51] Int. Cl.$^6$ .................................................. G01V 3/00
[52] U.S. Cl. .................................. 324/319; 324/320
[58] Field of Search ................................. 324/319, 320, 324/318, 322; 335/306, 299, 296

[56] References Cited

U.S. PATENT DOCUMENTS

| 4,695,802 | 9/1987 | Zijlstra | 324/319 |
| 4,703,276 | 10/1987 | Beer | 324/319 |
| 5,467,769 | 11/1995 | Yoshino et al. | 324/318 |

*Primary Examiner*—Louis M. Arana
*Attorney, Agent, or Firm*—Watson Cole Stevens Davis, PLLC

[57] ABSTRACT

A magnet field generating apparatus for MRI, comprising: a plurality of permanent magnet assemblies disposed continuously around the angular inner circumference of a hexagonal tubular yoke to provide a uniform magnetic field at the center portion of the hollow space inside said permanent magnet assemblies; the permanent magnet assemblies forming a main magnetic field by a pair of oppositely disposed permanent magnet assemblies which are trapezoidal or square in cross-section; other pairs of permanent magnet assemblies having a triangular or square cross-section; each of the pairs of oppositely disposed permanent magnet assemblies has a side surface in contact with a part of the inner peripheral surface of the yoke and forms a plurality of permanent magnet blocks which are magnetized perpendicularly to the side surface in contact with the yoke so that the permanent magnet assemblies are magnetized perpendicularly to the side surface thereof in contact with the yoke; magnetic pole pieces disposed on each surface of the pair of oppositely disposed permanent magnet assemblies; and permanent magnet piece projections having the same magnetizing direction as the plurality of permanent magnet assemblies are respectively disposed on each surface of the paired oppositely disposed permanent magnet assemblies on which no magnetic pole piece is disposed.

25 Claims, 13 Drawing Sheets

MAGNETIC FIELD GENERATOR FOR MRI

TECHNICAL FIELD

The present invention relates to improvement of a magnetic generating apparatus used in a magnetic resonance imaging (hereinafter referred to as an MRI) and the like, particularly, it relates to a magnetic field generating apparatus having a good magnetic effect, which is constituted by disposing a plurality of permanent magnet constituents along the inner surface of a polygonal tubular yoke, and is easy to assemble by directing a magnetizing direction of a plurality of permanent magnet blocks constituting the permanent magnet constituents in a specific direction.

TECHNICAL BACKGROUND

An MRI is a system, wherein a portion or an entire subject is inserted into a hollow space of a magnetic field generating apparatus forming a strong magnetic field to obtain a tomographic image of the subject, thereby to draw out even characteristics of the tissue.

The hollow space of the magnetic generating apparatus must be so large that the porting or entire subject can be inserted, and for the purpose of obtaining the clear tomographic image, usually, it is necessary to form a strong stable uniform magnetic field having an accuracy of 0.22 to 2.0T or less at $1\times10^{-4}\Omega\cdot m$, in an image pickup visual field (in a spherical space of about 150 to 250 mm radius at the center porting of the hollow space).

As a magnetic field generating source of the magnetic field generating apparatus, though those using a superconductive magnet and as paraconductive magnet are known, in recent years, those using a permanent magnet are frequently used by the reason that, the apparatus has a relatively simple configuration and the running cost is low.

As the magnetic field generating apparatus for MRI using the permanent magnets as the magnetic field generating source, a configuration, in which a pair of permanent magnet constituents opposing one another as forming a hollow space are connected by a yoke as shown in the U.S. Pat. No. 4,672,346(EP 0161782 B1) is widely adopted.

In the above-mentioned magnetic field generating apparatus, the permanent magnet constituents are usually constituted by a plural number of permanent magnet blocks by the reason of manufacturing problems and assembling workability.

In this configuration, since a magnetizing direction of the permanent magnet constituents is in the same direction as a direction of magnetic field in the hollow space, and also a transverse cross section is substantially a square, a direction of thickness of the permanent magnet constituents is the magnetizing direction, thus it is easy to assemble by laminating and integrating the plural number of cubical or rectangular parallel-piped permanent magnet blocks having the magnetizing direction in the direction of thickness.

While, a configuration, in which a plural number of permanent magnet constituents are disposed angularly, and an uniform magnetic field is formed at a center portion in the permanent magnet constituents, is known (U.S. Pat. No. 4,498,048, EP 0120927 B1 and Japanese Patent pablication No. Hei 4-10334).

In the magnetic field generating apparatus having such configuration, since respective permanent magnet constituents have, for example, a sectionally trapezoid shape, and the direction of magnetic field in the hollow space differs form the magnetizing direction of the permanent magnet constituents depending on locations where the permanent magnet constituents are arranged, in order to obtain a desired magnetizing direction, the permanent magnet blocks must be formed into a specific shape, or at the time of their magnetization, a magnetizer capable of positioning the permanent magnet constituents very precisely is required, results in a very complicated assembling work.

As the configuration for solving such problem, a configuration, in which a plurality of bar-shaped permanent magnet constituents having a triangular or substantially square and triangular transverse section are disposed angularly along the inner surface of a polygonal tubular yoke, is proposed (U.S. Pat. No. 4,695,802, EP 0170318 B1 and Japanese Patent publication No. Hei 4-75008).

As compared with the configuration, in which a pair of permanent magnet constituents are oppositely disposed in the yoke as forming the hollow space, in this configuration, though, a magnetic leakage is little and the permanent magnets can be used effectively, since the magnetizing direction of the permanent magnet constituents having a triangular transverse section is that, the permanent magnet blocks magnetized respectively in the direction of thickness are overlapped one another so as to have the different magnetizing directions, for example, to have the magnetizing directions which differ form each other by 90 degrees, and the magnetizing direction as the entire permanent magnet constituents are brought in parallel (same direction) and/or perpendicularly to the direction of the magnetic field in the hollow space, it is not always effective from a viewpoint of assembling work and is not practically used.

Furthermore, as an improved magnetic field generating apparatus of the configuration, in which the pair of the permanent magnet constituents are opposing disposed in the yoke as forming the hollow space (U.S. Pat. No. 4,672,346) and the configuration, in which the plurality of permanent magnet constituents are disposed angularly and the uniform magnetic field is formed at the center in the permanent magnet constituents (U.S. Pat. No. 4,498,048), the configuration, in which a pair of permanent magnet constituents consisting of a trapezoid transverse section and a permanent magnet constituent consisting of a scalene triangular transverse section are connected in a picture-frame shape, or the oblique side of the trapezoid permanent magnet constituent and the short side of the scalene triangular permanent magnet constituent are contacted closely along the inner surface of the polygonal tubular yoke, is proposed (Japanese Patent application Laid Open No. Sho 62-177903).

A configuration, in which permanent magnet pieces for correcting non-uniform magnetic field are disposed on both axial ends of the trapezoid permanent magnet constituent and the scalene triangular permanent magnet constituent, is also proposed (Japanese Patent Application Laid Open No. Sho 63-43304).

However, in these configuration, the trapezoid permanent magnet constituent, scalene triangular permanent magnet constituent and the non-uniform magnetic field correcting permanent magnet pieces are all characterized by having the magnetizing direction which is perpendicular to the boundary face with the hollow space (opposite faces in the hollow space), and among the permanent magnet blocks constituting the individual permanent magnet constituent, the permanent magnetic constituent in the vicinity of the contact with the yoke is complicated to be processed, magnetized and assembled from a viewpoint of its magnetizing direction.

Also, since the permanent magnet constituents are closely disposed one another in the picture-frame shape as previously described, the permanent magnet constituents magnetically repulse one another at the close-contact portion, thus it is problematic from the safety point of view, and further, reproducibility of obtaining the desired magnetic field uniformity always at a mass production is also problematic.

It is, therefore, a primary object of the present invention to provide a magnetic field generating apparatus having a good magnetic efficiency, in which an advantage inherent to a magnetic field generating apparatus for MRI constituted by disposing a plurality of permanent magnet constituents angularly along the inner surface of a polygonal tubular yoke is adopted positively, particularly, a magnetizing direction of a plural number of permanent magnet blocks constituting the permanent magnet constituents is directed in a specific direction to facilitate the assembling work, and the desired magnetic field uniformity is always obtained with good reproducibility at a mass production.

It is another object of the present invention to provide a magnetic field generating apparatus, in which permanent magnet constituents and a yoke capable of reducing generation of eddy currents influenced due to gradient magnetic field coils, and further, magnetic polar pieces capable of reducing generation of the eddy currents and improving the magnetic field uniformity are arranged.

It is a further object of the present invention to provide a magnetic field generating apparatus, in which by devising the arrangement of permanent magnet constituents generating the magnetic field most efficiently in the hollow space, and the shape of permanent magnet constituent itself, the magnetic field uniformity is further improved.

DISCLOSURE OF THE INVENTION

By positively utilizing an advantage inherent to a magnetic field generating apparatus for MRI, constituted by disposing a plurality of permanent magnet constituents angularly along the inner surface of a tubular yoke, or the advantage of facilitating generation and concentration of the magnetic field at the center in the yoke, we have made various studies for the purpose of constituting the magnetic field generation apparatus, which is easy to assemble and has a good reproducibility, and further, capable of further improving the magnetic field uniformity in a spherical space of a predetermined size set in an image-pickup visual field, and enhancing the using efficiency of magnets.

As the result, we have found out that, by bringing the magnetizing direction of the permanent magnet constituents perpendicularly to the contact face with the yoke, or bringing the magnetizing direction of the plural number of permanent magnet blocks constituting the permanent magnet constituents perpendicularly to the contact face with the yoke and assembling in a same direction, the permanent magnet constituents can be assembled easily, and the magnet efficiency is improved for lightening the apparatus, and further, found out that, from the fact that the permanent magnet constituents can be assembled with a good reproducibility, when combining with means for reducing magnetic flux leakages at an opening of a magnetic circuit, and various means for improving the magnetic field uniformity at desired portions, it is possible to evaluate the adopted means and to confirm the effects, thereby conditions of the adopted means can be optimized further and the magnetic field uniformity can be improved efficiently by multiplier effects.

Particularly described, when considering an optimum configuration of the permanent magnet being disposed angularly along the inner surface of the tubular yoke, it is considered to assemble by the subdivided magnet blocks to facilitate assembling into a desired shape, and further, from the magnet efficiency, anisotropic magnets are most suitable in all cases such as a ferrite magnet, a rare earth magnet and the like, in case of the anisotropic magnet, it is desirable to anisotropicize axially in an easily anisotropicizing direction from a viewpoint of manufacture.

By the way, we have invented that, by constituting such that, the magnetizing direction of the permanent magnet constituent is perpendicular to the contact face with the yoke, or by assembling the permanent magnet blocks having the magnetizing direction perpendicularly to the contact face with the yoke perpendicularly to the contact face with the yoke, the permanent magnet constituents can be assembled easily with a good reproducibility the using efficiency of the magnets is improved and the number of permanent magnets being used can be decreased.

Meanwhile, in order to improve the using efficiency of the magnets for miniaturizing and lightening the magnetic field generating apparatus, though it is preferable to use R-Fe-B type anisotropic magnets (where, R is, at least, one kind of Nd, Pr, Dy, Ho, Tb, La, Ce, Gd and Y) which is, at present, the magnet having the highest performance and characteristics of 30 MGOe or more maximum energy product, however, the permanent magnet constituent of the R-Fe-B type magnet exposed directly to the gradient magnetic field is problematic in that, eddy currents are generated in the permanent magnet, because the electric specific resistance is small and about $10^{-6}\Omega\cdot m$.

That is, in the magnetic field generating apparatus for MRI, positional information is usually transferred to nuclear magnetic resonance signals by giving the the inclined magnetic field to the uniform magnetic field, and it is necessary to change a number of pulse magnetic fields to obtain an image. Though the inclined magnetic field is generated by applying a pulse current to the gradient magnetic field coils, when there is a conductor such as iron in its vicinity, the eddy current is generated and the gradient magnetic field can not rise rapidly.

By the way, though the permanent magnet constituent may have any shapes and configurations responding to the polygonal tubular yoke, when the permanent magnet constituent is formed by laminating the plural number of permanent magnet blocks having the different sizes, in case the specific resistance of the permanent magnet blocks is $10^{-3}\Omega\cdot m$ or less as the R-Fe-B type anisotropic magnet, by constituting the permanent magnet constituent by the plural number of permanent magnet blocks which are electrically insulated from each other, the eddy current generated in the permanent magnet constituent can be reduced.

When assembling such permanent magnet constituents, the respective permanent magnet blocks are preferably electrically insulated completely, the electrical insulation in a desired direction is preferably considered responding to the shape of the permanent magnet block, so as to increase the specific resistance at least the faces in parallel to the opposite faces of the hollow space in the permanent magnet constituents, after completion of the assembling, particularly, when assmbling the permanent magnet blocks having the magnetizing direction perpendicularly to the contact face with the yoke, perpendicularly to the contact face with the yoke, by electrically insulating the contact face with the adjoining permanent magnet blocks positioned at right angles to the magnetizing direction of the permanent magnet blocks, the permanent magnet constituents are electrically insulated at right angles to the magnetizing direction of respective permanent magnet blocks, results in a high apparent specific resistance and a higher suppressive effect on the eddy currents.

Insulating means of the permanent magnet blocks is that, in order to electrically insulate, at least, the contact face with the other permanent magnet blocks adjoining at right angles to the magnetizing direction of the respective permanent magnet blocks, besides providing, beforehand, a resin coating of epoxy resin and the like and an insulating film of electrodeposition painting and the like on respective contact faces with the permanent magnet blocks, insulating adhesives may be coated on the contact face when assembling to the permanent magnet constituent, the insulating materials are not restricted to the aforesaid examples as far as they are non-conductive.

As to above-mentioned electrical insulations between such permanent magnet blocks, specific resistance are preferably, at least, $10^{-3}\Omega \cdot m$ in specific resistance, and the thickness of the insulating film is preferably above 10 µm.

Though such electrical insulation is not necessary in the case of ferrite magnet where the specific resistance of the permanent magnet block exceeds $10^{-3}\Omega \cdot m$, in the case of using the permanent magnet such as an alnico magnet, a rare earth cobalt magnet and the like, and particularly, high performance R-Fe-B type magnets for obtaining a stable and uniform magnet field to minimize the apparatus, the specific resistance of the permanent magnet block is preferably below $10^{-3}\Omega \cdot m$, and the electrical insulating means is, preferably provided on the permanent magnet block.

Though various shapes and sizes of the permanent magnet block may be selected depending on the forms and sizes of the magnet field generating apparatus, particularly, in order to enhance reduction effects of the eddy currents, the permanent magnet block is preferably a small block having the longest side length of 100 mm or less.

The ferrite magnet, alnico magnet, cobalt magnet and R-Fe-B type magnet blocks are used for the permanent magnet block, for the stable magnetic field uniformity and the miniaturization of the apparatus, taking into consideration of the handling during the aforementioned assembling and mechanical characteristics, besides the required a magnetic and electric characteristics, it is desirable to select the most suitable material, shape and size.

In the present invention, a magnetic circuit is constituted such that, permanent magnet constituents of triangular, trapezoid or square sections are combined into a polygonal tubular shape, and disposed, in a body, along the inner surface of a polygonal tubular yoke such as a hexagonal tubular yoke. By this configuration, the magnetic leakage is reduced and the magnets can be used efficiently.

In the present invention, as the polygonal tubular yoke, along the inner surface of which the permanent magnet constituents are disposed, besides a bulk of iron and the like, a laminate of silicon steel plates, iron and the like may be used, and particularly, by using the silicon steel plates, reduction effects of the eddy currents generated in the yoke is improved. The silicon steel plates being laminated may be those used usually and having the thickness of 0.35 mm, 0.5 mm and so on.

In the present invention, in the case of constituting the entire yoke with the laminated silicon steel plates, for preventing the change in magnetic field which becomes weaker in a direction (in a direction of z-axis) aparting from the center of the permanent magnet constituent dye to the magnetic flux leakages from an opening, for example, by dividing the polygonal tubular yoke in a direction of depth, uniform magnetic field distributions can be obtained.

Though generation of the eddy currents may be reduced by constituting the entire tubular yoke with the laminated silicon steel plates, the mechanical strength of the yoke is weakened on the other hand, and it takes much time for assembling. Thus, various configurations may be selected such as disposing the laminated silicon steel plates only at the contact portion with the permanent magnet constituents, without constituting the entire yoke with the silicon steel plate. For example, in a configuration wherein magnetic pole pieces to be described later are provided on a pair of permanent magnet constituents for forming a main magnetic field opposing as forming a hollow space, by constituting such that, the main yoke body is formed by a bulk material and the laminated silicon steel plates are disposed at the contact portion with the permanent magnet constituents where the magnetic pole pieces are not provided, generation of the eddy currents can be reduced without deteriorating the magnetic field uniformity in the hollow space, results in the configuration which is easy to process and manufacture and superb in the assmbling workability.

As described above, the present invention is characterized in that, the magnetizing direction of the plural number of permanent magnet constituents disposed angularly along the inner surface of the polygonal tubular yoke is constituted perpendicularly to the contact face with the yoke, or by constituting the plural number of permanent magnet constituents disposed along the inner surface of the yoke by laminating the permanent magnet blocks having the magnetizing direction perpendicularly to the contact face with the yoke, the permanent magnet constituents can be assembled easily, the magnetic field uniformity of the desired portions is improved and the amount of permanent magnets to be used can be decreased.

Furthermore, the present invention is characterized in that, the plural number of permanent magnet constituents disposed along the inner surface of the polygonal tubular yoke are constituted by the permanent magnet blocks having the magnetizing direction perpendicularly to the contact face with the yoke, and when forming the uniform magnetic field in the center of the hollow space in the permanent magnet constituents, by forming a main magnet field by the pair of permanent magnet constituents having the magnetizing direction in the same direction as the magnetizing direction of the uniform magnetic field and disposed oppositely, the magnetic field uniformity in the tubular yoke can be improved. In such configuration, by forming gaps at adjoining portions of the pair of permanent magnet constituents forming the main magnetic field and the other permanent magnet constituents, the magnetic field uniformity in the tubular yoke can be improved remarkably.

Though the static magnetic field having a high magnetic field uniformity can be formed in the tubular yoke by the above-mentioned configuration, sometimes the higher magnetic field uniformity is required depending on use such as for the MRI, therefore, the present invention provides a configuration, wherein magnetic pole pieces are provided on the opposite faces in the hollow space of the pair of permanent magnet constituents which generate the main magnetic field, to satisfy such requirement or to use the magnets more efficiently.

Particularly, as the preferable configuration, for example, the magnetic pole pieces shorter than the permanent magnet constituent in a z-axis direction (an opening direction of the tubular yoke) are provided on the opposite faces in the hollow space of the pair of permanent magnet constituents, and projections are disposed in the center and/or both ends of the magnetic pole pieces, thereby the magnetic flux leakage at the openings is prevented and the length of the apparatus in an axial direction can be shortened.

In the present invention, in the configuration wherein the magnetic pole pieces are disposed on the pair of permanent magnetic constituents forming the main magnetic field, since gradient magnetic field coils are provided in the vicinity of the magnetic pole pieces, it is desirable to adopt the magnetic pole piece configuration descried in the following, for the purpose of reducing the eddy currents generated in the magnetic pole pieces.

That is, the silicon steel plates are preferably laminated, at least, on the opposite faces in the hollow space of the magnetic pole pieces in an opposing direction of the magnetic pole pieces, or in a direction at right angles to the opposing direction of the magnetic pole pieces, and when necessary, the laminating direction may be changed and lamineted plurality, or members for magnetic pole pieces may take various forms and assmbled in a desired shape.

Meanwhile, though the axial direction to facilitate magnetization of the silicon steel plate used as the members for magnetic pole pieces may have any directivity, in the case of constituting with non-oriented silicon plates (JIS C2552 etc.), remarkable effects are exerted in reducing a residual magnetism phenomenon.

Though the silicon steel plate may have any thickness, since the silicon steel plate which is obtained easily is, usually, thin and about 0.35 mm, for the purpose of easy lamination and good assembling workability, it is proposed to constitute such that, a plurality of block-shaped members for magnetic pole piece prepared by laminating a predetermined number of sheets of rectangular non-oriented silicon steel plates of a predetermined sizes in a direction at right angles to the opposing direction of the magnetic pole pieces are produced once, and the plural number of block-shaped members for magnetic pole pieces are fixed directly on the magnet constitutes, or through a magnetic base plate.

Also, for reducing the eddy currents generated in the magnetic pole pieces, soft ferrite may be disposed on the opposite faces in the hollow space of the magnetic pole pieces, in lieu of the silicon steel plate. The soft ferrite is composed of various soft ferrite materials such as Mn-Zn ferrite powder, Ni-Zn ferrite powder and the like, and the large soft ferrite blocks processed into a desired shape or the small blocks assembled into a desired shape by means of adhesives can be utilized.

When preparing the small soft ferrite block, for example, the Mn-Zn ferrite powder is sintered after being compressed and molded into a desired shape, and for improving the density, means such as HP and HIP (Hot Isostatic Pressing) methods may be commonly used, the resulting small blocks are assembled into the desired shape by bonding with adhesives such as an epoxy resin.

Among the soft ferrite materials, for example, the Mn-Zn soft ferrite has high permeability and high saturation induction Bs required as magnetic field uniforming means, and also has sufficiently high specific resistance as countermeasure for the eddy current and low coercive force Hc (several A/m) capable of preventing the residual magnetism phenomenon.

In the present invention, for effective action of the magnetic flux generated from the magnet constituent against the hollow space, the soft ferrite preferably has the saturation induction Bs of 0.4 T or more. That is, the amount of magnetic flux passing through the soft ferrite is determined by the Bs, and when the value is small, it is inevitably saturated and the magnetic field strength is weakened, thus it is necessary to enlarge the magnet to prevent this, results in a large apparatus. Thus, Bs is preferably above 0.4 T or 0.5 T, more preferably above 0.55 T.

Since the residual magnetism phenomenon occurs when Hc of the soft ferrite is too large, the Hc in preferably below 50 A/m or below 20 A/m, more preferably, below 10 A/m. For reducing the eddy currents, the specific resistance $\rho$ is preferably above $10^{-5}$ $\Omega\cdot$m, or more preferably above $10^{-3}$ $\Omega\cdot$m.

These soft ferrite blocks may also be fixed directly on the magnet constituent or through a magnetic base plate.

The block consisting of silicon steel plates and the block consisting of the soft ferrite may be used in composition, for example, by forming a surface layer of the magnetic pole pieces by the soft ferrite or the silicon steel plate, and forming a surface layer of the projections provided on opposite ends of the magnet pole pieces by the soft ferrite or the laminated silicon steel plate, the eddy currents and the residual magnetism phenomenon caused by the inclined magnetic field coils disposed in the vicinity of the magnet pole pieces can be reduced, without deteriorating the magnetic field strength and magnetic field uniformity, and further, the magnetic pole pieces can be processed and manufactured easily.

Magnetic field adjusting segments consisting of magnetic material or permanent magnet for fine adjustment of the magnetic field uniformity may be provided at desired positions of the magnetic pole pieces. Furthermore, by disposing a permanent magnet shim inclined by 30° to 60° so as to open the magnetizing direction toward the opening, at a bare portion of the magnet, where the magnetic pole piece is not disposed, on the opposite faces in the hollow space of the pair of permanent magnet constituents forming the main magnetic field, the magnetic field distribution in the hollow space can be further improved, and the using efficiency of the magnet can be improved.

BEST MODE FOR CARRYING OUT THE INVENTION

Embodiment 1

Figure 1:
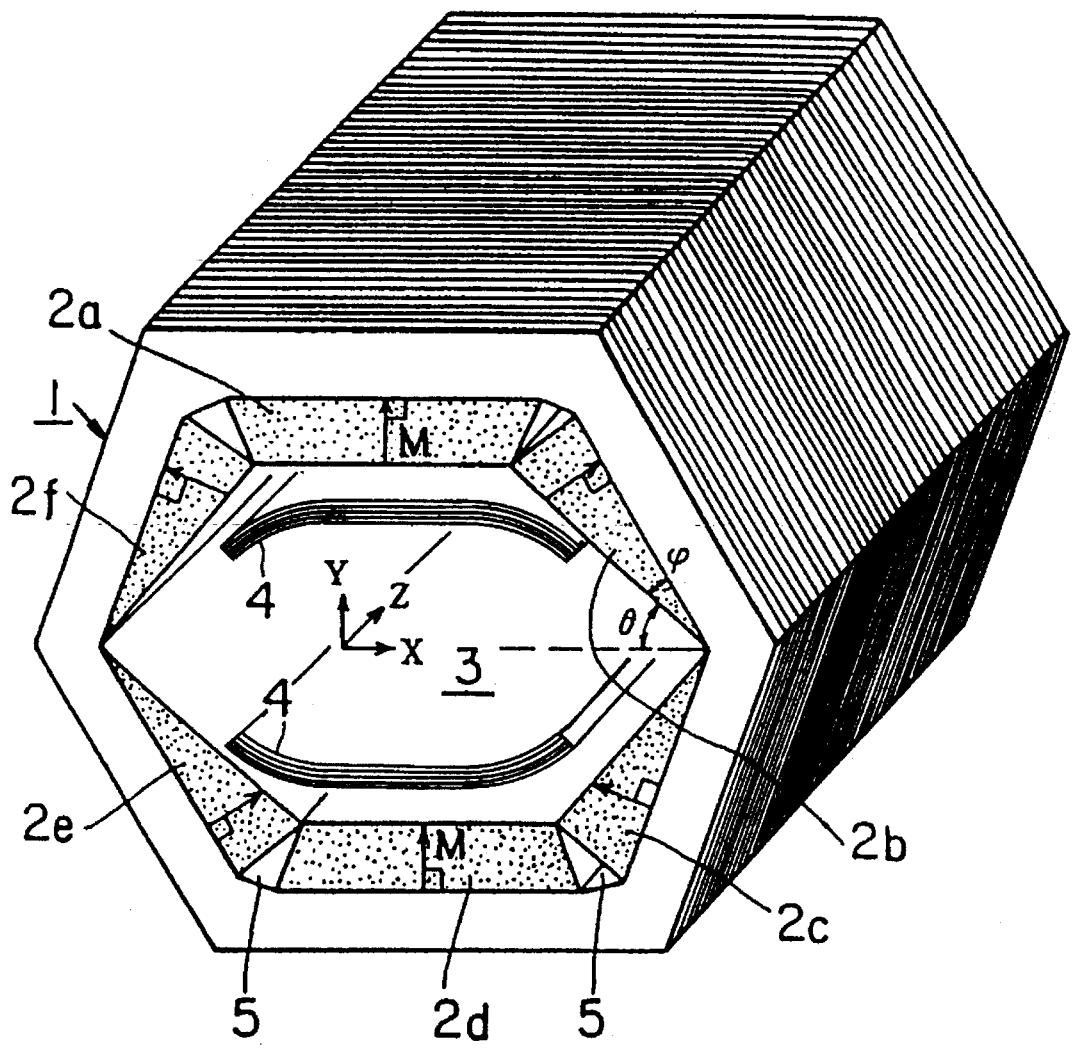
FIG. 1 is a perspective explanatory view showing a configuration of a magnetic field generating apparatus for MRI according to the present invention.

In FIG. 1, a pair of permanent magnet constituents $2a$, $2d$, whose opposite faces in a hollow space are formed at right angles to a predetermined magnetic field direction in the hollow space 3 in a polygonal tubular yoke 1, or disposed oppositely in a direction of y-axis along the inner surface of the polygonal tubular yoke 1, are a main magnetic field generating source, which is formed by assembling permanent magnetic blocks into a sectionally flat trapezoid plate shape, and contributes to formation of a magnetic field in the hollow space.

Meanwhile, a plurality of permanent magnet constituents $2b$, $2c$, $2e$ and $2f$ disposed along the remaining inner surface in the polygonal tubular yoke 1 are assembled into a sectionally triangular plate shape, the shape and size being selected suitably so as to generate a uniform static magnetic field in the hollow space 3.

Thus, a magnetic circuit is constituted by, disposing the pair of sectionally trapezoid permanent magnet constituents $2a$, $2d$, and the four sectionally triangular permanent magnet constituents $2b$, $2c$, $2e$ and $2f$ forming the main magnet field angularly along the inner surface of the tubular yoke 1 and integrating magnetically.

Magnetizing directions (shown by arrows in the figure) of all permanent magnet constituents are constituted so as to be perpendicular to the contact face of the yoke. That is, as to described later, the plurality of permanent magnet blocks themselves constituting the permanent magnet constituents are magnetized perpendicularly to the contact face of the yoke.

Figure 2:
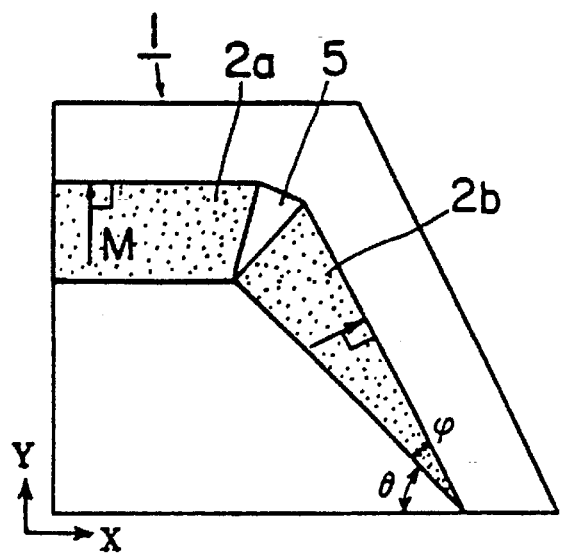
FIG. 2 is an explanatory view of essential portions showing a configuration of an adjoining gap between permanent magnet constituents of a magnetic field generating apparatus for MRI according to the present invention.

Though various shapes are selected for the sectionally triangular permanent magnet constituents $2b$, $2c$, $2e$ and $2f$ depending on a desired magnetic induction (Bg) in the hollow space, the size of hollow space and so on, as shown in FIG. 2, usually, an angle $\psi$ is set by taking into account of magnetic characteristics of the permanent magnet, $\theta$ and Bg, and a shape and size of the yoke are decided in response thereto. The inventor has succeeded in forming a desirable magnetic field when $\theta$ is in the range from 45° to 90°, and particularly, most preferably at 45°.

However, in all cases, when the permanent magnet blocks are disposed and laminated perpendicularly to the contact face of the permanent magnet constituent with the yoke, its magnetizing direction can be easily arranged so as to be perpendicular to the contact face with the yoke.

Particularly, as shown in FIG. 2, by forming an adjoining gap 5 between the sectionally trapezoid permanent magnet constituent $2a$ and the sectionally triangular permanent magnet constituent $2b$, or at an circumferential adjoining portion in the yoke 1, the magnetic field uniformity in the polygonal tubular yoke 1 can be improved remarkably.

Figure 3:
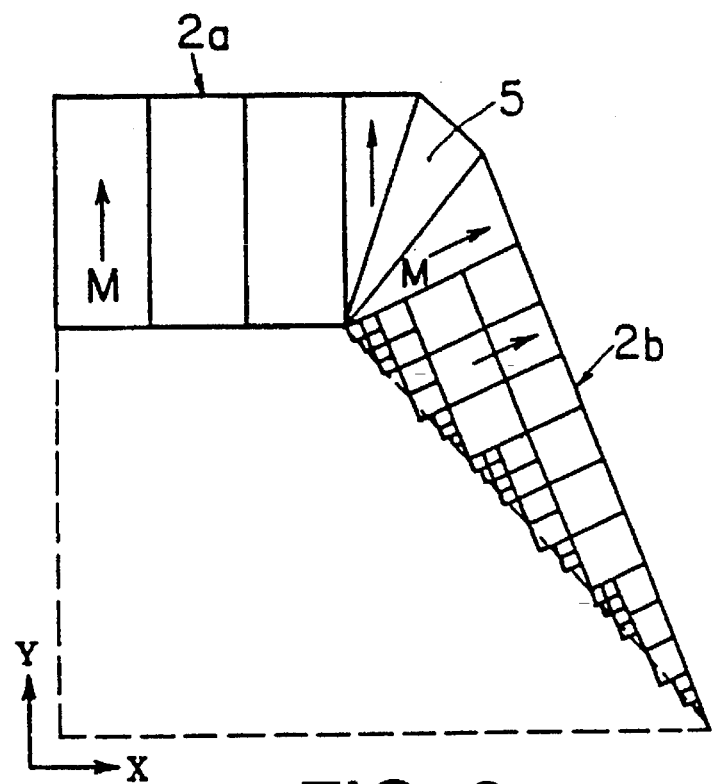
FIG. 3 is a explanatory view of essential portions showing an assembled configuration of permanent magnet constituents of a magnetic field generating apparatus for MRI according to the present invention.

Though a shape of the adjoining gap 5 is decided by selecting suitably, depending on the shape and size of the both permanent magnet constituents $2a$, $2b$ and the yoke 1, as shown in FIG. 3, by disposing permanent magnet blocks, whose shape and size are selected diversely, at the adjoining portions of the permanent magnet constituents $2a$, $2b$, a uniform static magnetic field is obtained also in the adjoining gap 5, and the magnetic field uniformity in the polygonal tubular yoke 1 is improved.

Though an example of a permanent magnet block assembly in the permanent magnet constituents $2a$, $2b$ is shown in FIG. 3, the permanent magnet constituents are not necessarily constituted by the same size permanent magnetic blocks or formed into perfect sectionally triangular plates, for example, the permanent magnet blocks which are formed into various shapes and sizes such as substantially trapezoid plates and magnetized perpendicularly (direction of allows M in the figure) to the contact face of the permanent magnet constituents with the yoke, are preferably laminated perpendicularly to the contact surface of the yoke to form the substantially triangular permanent magnet constituents.

In the case where the shape of the opposite faces of the permanent magnet constituents in the hollow space are inclined and the sectionally triangular permanent magnet blocks are necessary, since it is constituted such that the permanent magnet blocks magnetized perpendicularly to the contact face of the permanent magnet constituents with the yoke are disposed and laminated perpendicularly to the contact face of the yoke, the sectionally triangular permanent blocks can be manufacture easily without changing the magnetizing direction inherent to the permanent magnet, on the basis of a permanent magnet block laminate section or an end face parallel to the contact face of the yoke, In the above configuration, in the case of using a high performance R-Fe-B type magnet having a specific resistance below $10^{-3}$ Ω·m in the permanent magnet blocks constituting the permanent magnet constituents, for reducing generating of eddy currents due to effects of gradient magnetic field coils disposed in the vicinity of opposite faces of the permanent magnet constituents in the hollow space, the permanent magnet blocks are, preferably, electrically insulated by means of insulating adhesives and the like.

The magnetic field generating apparatus for MRI according to the present invention is easy to assemble, by making the magnetizing direction of the plurality of permanent magnet blocks constituting the permanent magnet constituents of the magnetic circuit, perpendicularly to the contact face of the permanent magnet constituents with the yoke, and further, the using efficiency of the magnets is improved, so that the entire magnetic circuit can be lightened.

Eddy current characteristics produced in the magnetic circuit, in which the gradient magnetic field coils 4 are disposed in the hollow space 3 which is formed by using the hexagonal tubular yoke 1 consisting of silicon steel laminates shown in FIG. 1, and disposing 6 types of permanent magnet constituents 2a to 2f along the inner surface of the yoke 1, are evaluated by applying a sine-wave current to the gradient magnetic field coils and changing the frequency to measure a generated magnetic field by an electromotive force generated in a search coil provided in the hollow space. The sine-wave current in this case is 450 A·T.

Here, the permanent magnet constituents are that, a plurality of R-Fe-B type magnet blocks having, mainly, the size of 36 mm×40 mm×40 mm and a maximum energy product of 35 MGOe are electrically insulated from each other for integration.

Embodiment 2

In the same configuration as the Embodiment 1, the entire yoke is formed into a polygonal tubular yoke consisting of a bulk soft iron, and the generated magnetic field at the time of applying a sine-wave current, similarly, to the gradient magnetic field coils is measured for evaluation.

In the following embodiment, the magnetizing direction of the permanent magnet block is same as the Embodiment 1 unless otherwise specified.

Comparative Example 1

As same as the Embodiment 2, the yoke is formed into a polygonal tubular yoke consisting of a build soft iron such as iron, and measured as same as the Embodiment 1 without insulating respective permanent magnet blocks of the permanent magnet constituents.

Figure 4:
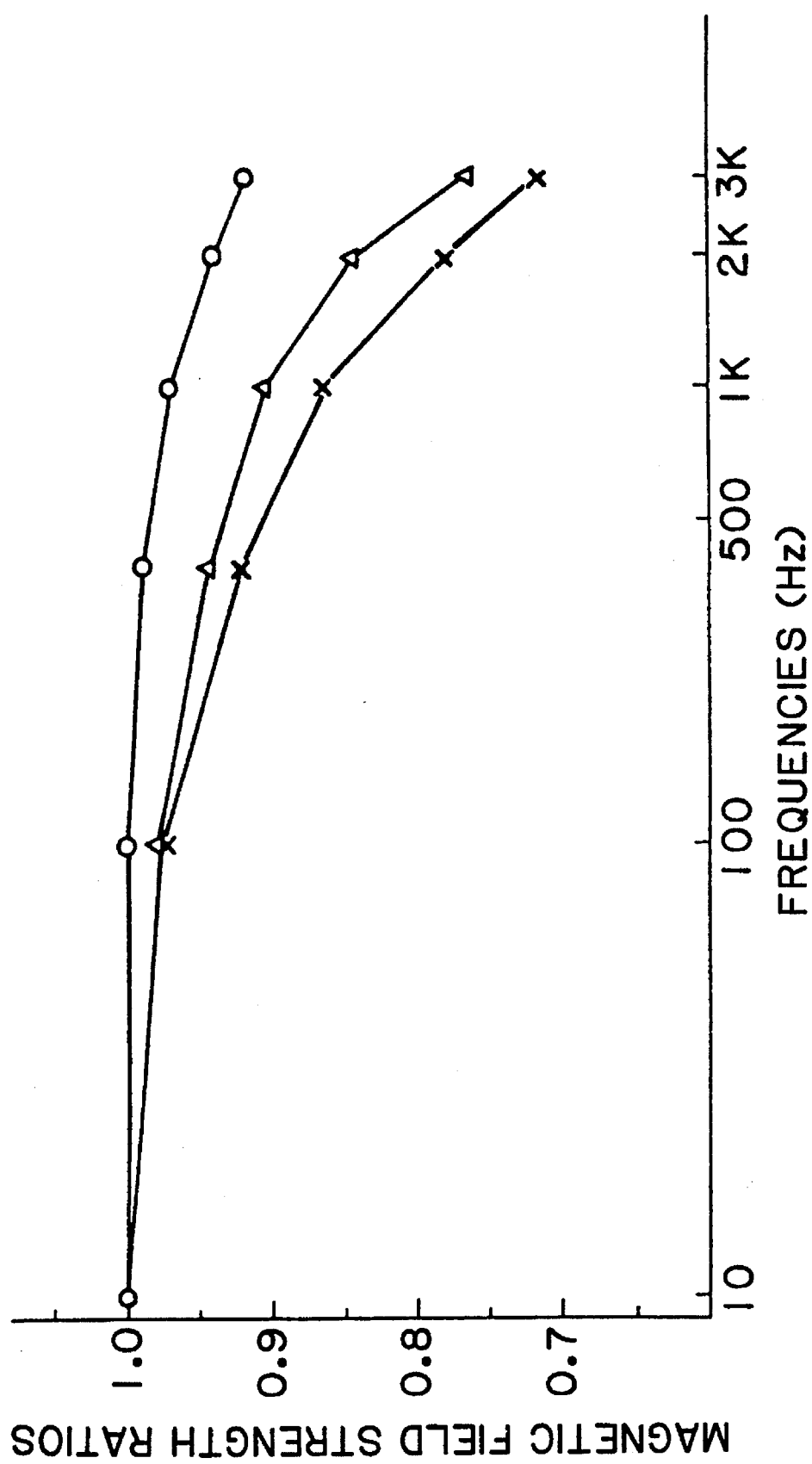
FIG. 4 is a graph showing the relationship between frequencies and magnetic field strength ratios in embodiments of the present invention.

The measured results are shown in FIG. 4 as the relationship between frequencies and magnetic field intensity ratios. As it is apparent from FIG. 4, against the Comparative Example 1 (plotted by marks ) in which the permanent magnet blocks are not insulated, in the case of Embodiment 2 (plotted by marksΔ)of the present invention in which the permanent magnet blocks are insulated, from the fact that the magnetic field intensity ratio is fiat till a high frequency region, it is understood that the generation of eddy currents is suppressed.

Also, in the case of Embodiment 1 (plotted by marks ) in which the entire yoke is constituted by silicon steel plate laminates, it is understood that, as compared with the Embodiment 2, the magnetic field intensity ratio does not drop even the frequency increases, and the generation of eddy currents is further suppressed.

It is understood that, in the aforesaid configuration, the magnetic field uniformity of 30 ppm is obtained in a measurement space within a 200 mm radius from the center of the hollow space, and a residual magnetism is also at an acceptable level.

Embodiment 3

Figure 5:
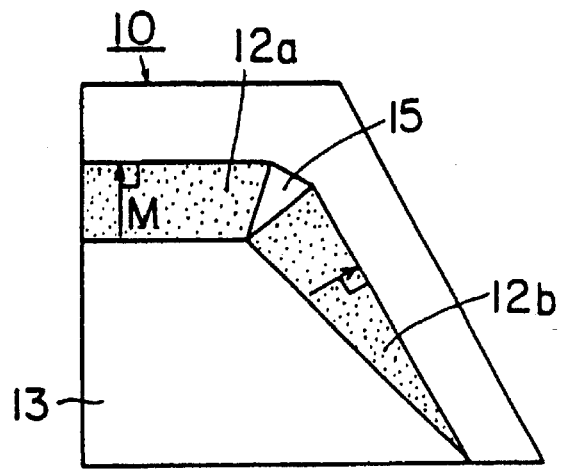
FIG. 5 is an explanatory view of essential portions showing a magnetizing direction of permanent magnet constituents of a magnetic field generating apparatus for MRI according to the present invention.

As the magnetic field generating apparatus of the present invention; on opposite faces of a hollow space 13 in a tubular yoke 10 consisting of a hexagonal tubular iron bulk having the thickness 90 mm and the length of 1300 in a z-axis direction, as FIG. 5 showing a quarter portion in x-y axis directions in the venter of the hollow space at an opening of the hexagonal tubular yoke, a pair of permanent magnet constituents 12a consisting of sectionally trapezoid R-Fe-B type anisotropic magnets, having the width of 520 mm, the thickness of 170 mm and the length of 1300 mm in the z-axis direction, and the magnetizing direction perpendicularly to the opposite faces in the hollow space, which is the inner surface of the yoke 10,for generating a main magnetic field, are disposed oppositely.

For generating a uniform static magnetic field in the hollow space 13, on the opposite faces in the hollow space of the yoke 10, a permanent magnet constituent 12b having the magnetizing direction perpendicularly to the contact face of the yoke, and consisting of four pieces of sectionally triangular R-Fe-B type anisotropic magnets is disposed, and an adjoining gap portion 15 is provided between the permanent magnet constituents 12a and 12b for integration, Comparative Example 2

Figure 6A:
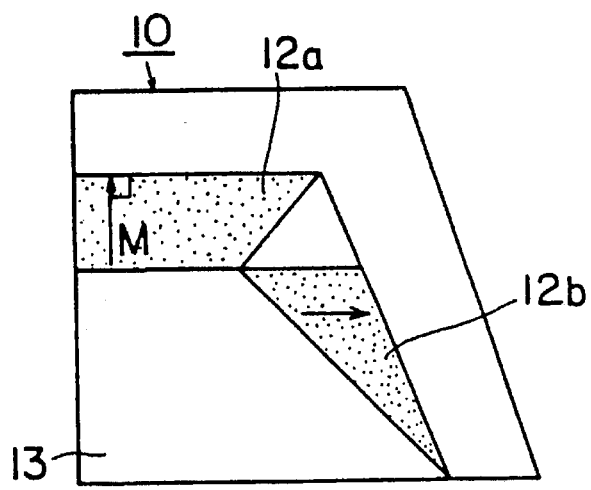
FIG. 6 (A) and (B) are explanatory views of essential portions showing a magnetizing direction of permanent magnet constituents of a conventional magnetic field generating apparatus for MRI.
Figure 6B:
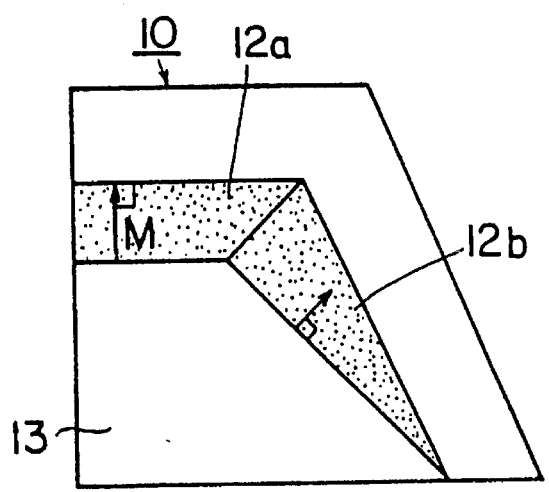

In the same configuration as the Embodiment 3, as shown in FIG. 6 (A), a magnetic field generating apparatus having a configuration (Comparative Example 2), in which the magnetizing direction of the four sectionally triangular permanent magnet constituents 12b besides the pair of permanent magnet constituents 12a forming the main magnetic field is arranged in parallel to the x-axis, is prepared.

In the same configuration as the Embodiment 3, as shown in FIG. 6 (B), a magnetic field generating apparatus having a configuration (Comparative Example 3), in which the magnetizing direction of the four sectionally triangular permanent magnet constituents besides the pair of permanent magnet constituents forming the main magnetic field is arranged perpendicularly to the opposite faces of the hollow space, is prepared.

Weights of the magnets of the magnetic circuits in the Embodiment 3, Comparative Example 2 and Comparative Example 3, constituted so as to obtain a magnetic field uniformity of 30 ppm in a measurement space within the 200 mm radius from the center of the hollow space, are shown in Table 1. The weights of magnets are compared by weight per meter in the z-axis direction.

As it is apparent in Table 1, the weight of the magnets of the permanent magnet constituents of the embodiment according to the present invention can be reduced by 8.2% from the weight of the magnets of the Comparative Example 2 and by 2.5% from that of the Comparative Example 3.

TABLE 1

|  | Embodiment 3 | Comparative Example 2 | Comparative Example 3 |
| --- | --- | --- | --- |
| Weight (ton/m) | 2.68 | 2.92 | 2.75 |

Embodiment 4

Figure 7:
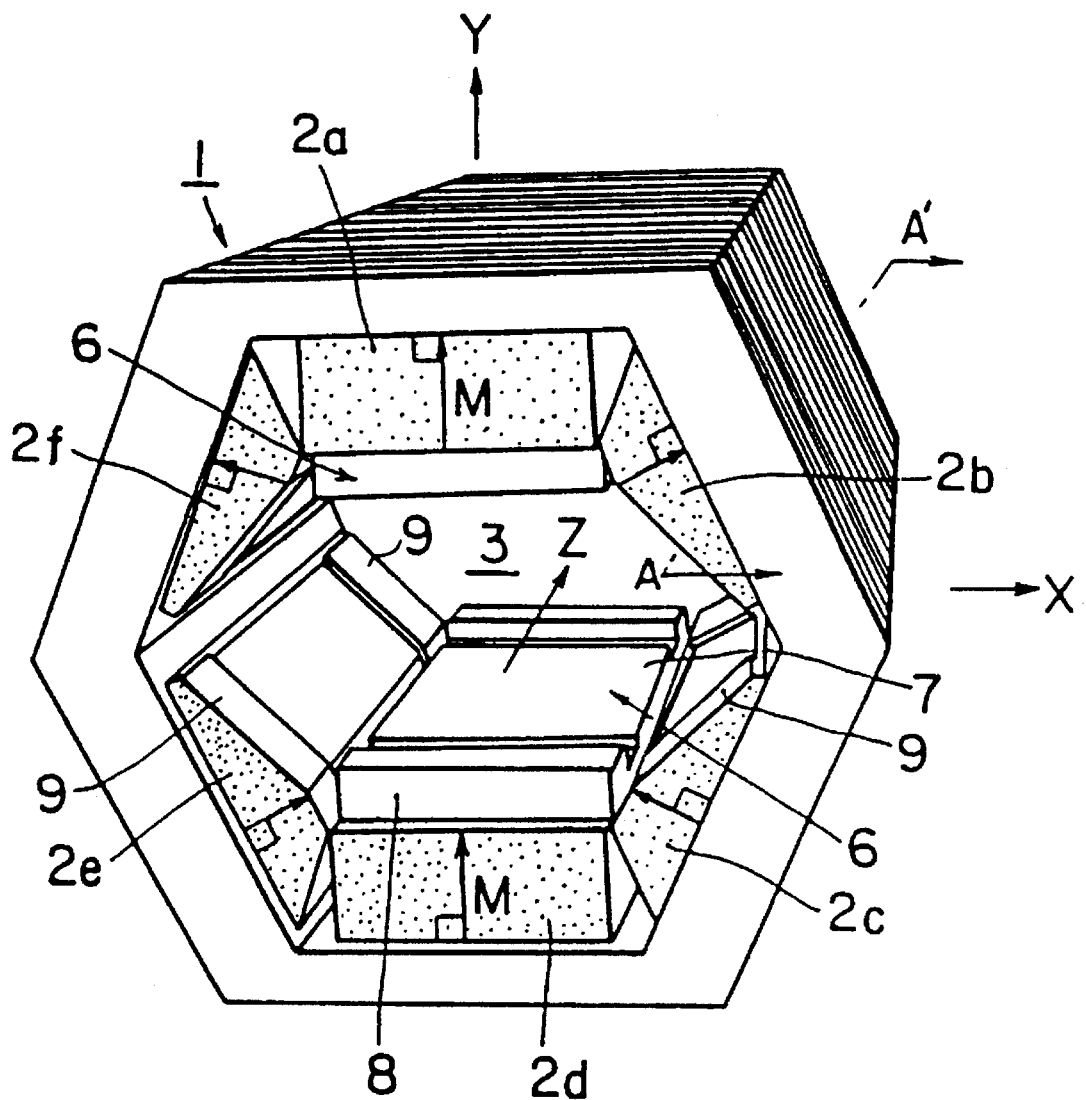
FIG. 7 is a perspective explanatory view showing another configuration of a magnetic field generating apparatus for MRI according to the present invention.

A configuration of a magnetic circuit shown in FIG. 7 is that, as same as the configuration shown in FIG. 1, permanent magnet constituents are disposed along the inner surface of a tubular yoke 1 consisting of silicon steel plate laminates, and a pair of permanent magnet constituents 2a, 2d serving as a main magnetic field generating source and contributing to formation of the magnetic field in the hollow space, usually have the magnetizing direction (indicated by allows M in the figure) in a magnetic field direction Y in the hollow space 3, thereby to form the opposite faces in the hollow space. The magnetizing direction of the other sectionally trapezoid permanent magnet constituents 2b, 2c, 2e and 2f are arranged so as to be perpendicular to the contact face of the yoke.

On the opposite faces in the hollow space of the pair of permanent magnet constituents 2a, 2d forming the main magnetic field, magnetic pole pieces 4, 4 are disposed and fixed to the yoke 1, through the magnet, by means of bolts and the like. Though a shape of the magnetic pole piece may be selected diversely responsive to the configuration of the magnetic field and disposing positions on the permanent magnet constituents, the shape which is within the range of previously stated shapes of the magnetic pole piece, and capable of obtaining a uniform static magnetic field in the desired hollow space is used.

Though the thickness of the magnetic pole piece may be selected responsive to the magnetic field intensity of the hollow space, the material of the magnetic pole piece and the size of a uniform magnetic field space, it is preferably about 20 to 80 mm, more preferably, about 50 mm. The thickness T of the magnetic pole piece shown in FIG. 8 (A) includes the thickness of a center projection.

The length of the magnetic pole piece in an axial direction (z-axis direction) is preferably shorter than the total length L of the apparatus for preventing magnetic flux leakages, preferably about 1=0.8 L.

When sectional shapes of the permanent magnet constituents 2b, 2c, 2e and 2f, whereon the magnetic pole piece is not disposed, perpendicular to the z-axis are equal in the z-axis direction (in the direction of depth), wince the magnetic field intensity near the direction of 45° from the x-axis on an x-z axis plane is weakened, magnetic field distributions fluctuate in the desired space, results in deterioration of the magnetic field uniformity.

Since the uniform magnetic field space required in the hollow space 3 is a sphere or an elliptical sphere, in order to obtain the uniform magnetic field throughout the entire set space, shims 9 of a permanent magnet piece having the same magnetizing direction as the permanent magnet constituent are, preferably, disposed at both opposite end faces of the hollow space 3 at the opening portion of the permanent magnet constituents 2b, 2c, 2e and 2f whereon the magnetic pole piece is not disposed.

Figure 10:
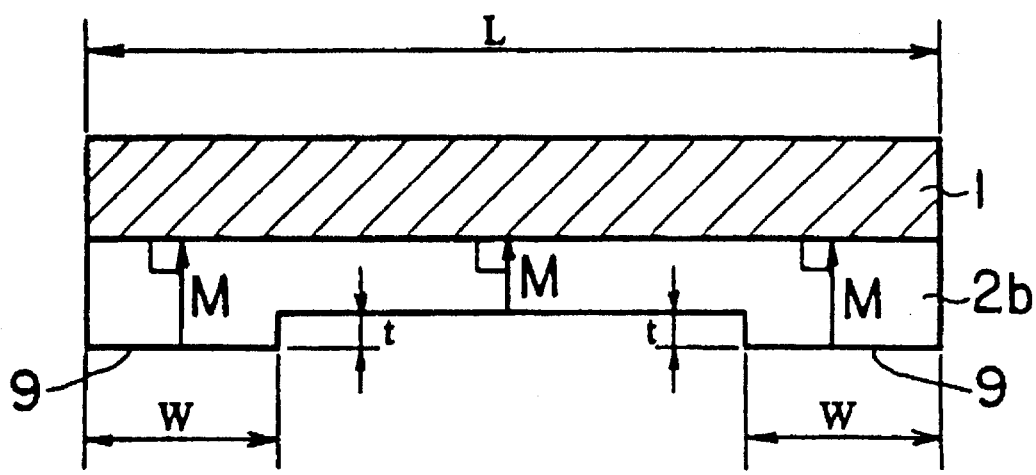
FIG. 10 is a schematic explanatory view showing a configuration of projections of a permanent magnet constituent, whereon a magnet pole piece is not disposed, according to the present invention.

Though the size of the shims 9 may be decided responsive to the magnetic field intensity in the hollow space and the size of desired uniform magnetic field space, as shown in FIG. 10, the length W in the axial direction (z-axis direction) is preferably about 0.2 L to 0.4 L, and the height t of the shim is preferably about 1 to 10 mm.

The shims 9 of the permanent magnet piece may be formed by partially thickening the thickness of the both ends of the permanent magnet constituents 2b, 2c, 2e and 2f, or by disposing permanent magnet pieces on the opposite faces in the hollow space of the permanent magnet constituents, the disposing method and shape may be selected suitably.

As same as the aforementioned configuration of FIG. 7, a pair of permanent magnet constituents having the same magnetizing direction and consisting of sectionally square R-Fe-B type anisotropic magnets generating the main magnetic field, are disposed oppositely on opposite faces in the hollow space of the yoke having the thickness of 90 mm and the length of 1300 mm in a z-axis direction and consisting of a hexagonal tubular iron bulk body, sectionally triangular permanent magnet constituents consisting of R-Fe-B type anisotropic magnets are disposed on the other opposite faces in the hollow space of the yoke.

Figure 8A:
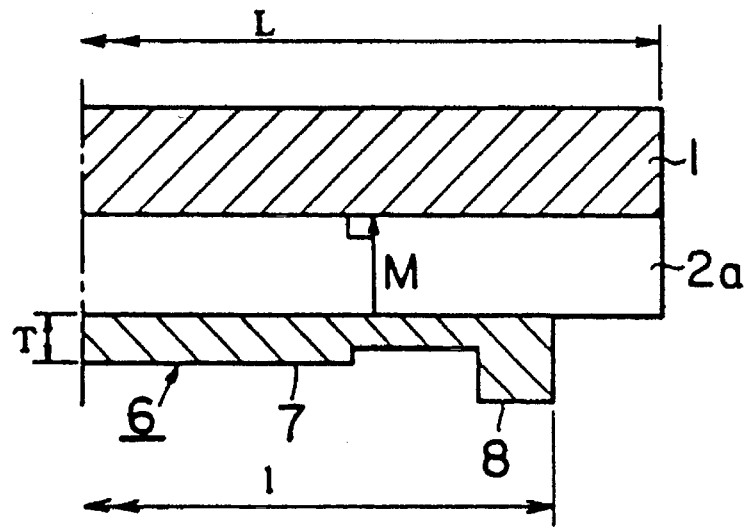
FIG. 8 (A) is a schematic explanatory view showing a configuration of a magnetic pole piece of a magnetic field generating apparatus for MRI according to the present invention, and (B) is a schematic explanatory view showing a permanent magnet constituent in which the magnetic pole piece is not disposed.
Figure 8B:
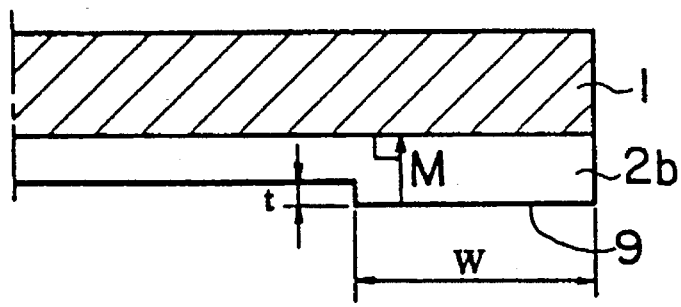

Magnetic pole pieces 6 having the thickness of 40 mm, the width of 520 mm and the length of 1050 mm in the z-axis direction, and constituted by laminating soft ferrites on a pure iron bulk having a desired size, are fixed to the opposite faces in the hollow space of the pair of permanent magnet constituents 2a, 2d generating the main magnetic field, the magnetic pole pieces 6 (T-50 mm), including projections 7 having the thickness of 10 mm and the length of 600 mm in the z-axis direction at the center portion thereof, and projections 8 as shown in FIG. 8 (A) having the thickness of 60 mm and the length of 80 mm in the z-axis direction at its both ends at the opening portion of the apparatus, are provided.

Furthermore, on the both end faces of the opening portion of the permanent magnet constituents 2b, 2c, 2e and 2f facing the hollow space 3, projections 9 as shown in FIG. 8 (B), taken along the line A—A' in FIG. 7, having the length 320 mm in the z-axis direction and the height 5 mm are disposed.

Figure 12A:
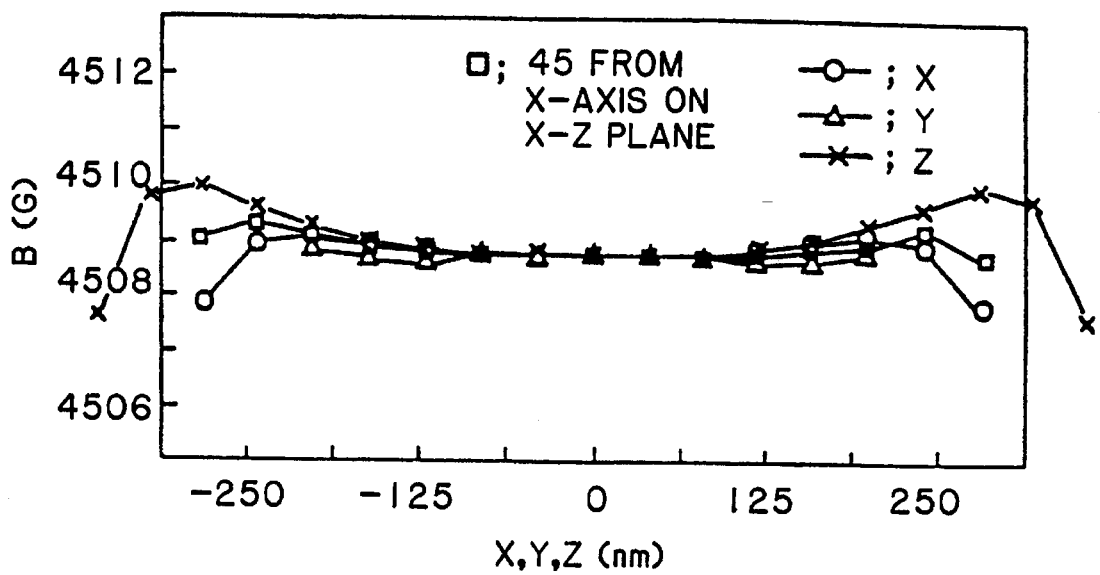
FIG. 12 is a graphs showing magnetic field distributions corresponding to directions of x-axis, z-axis and 45° from x-axis on an x-z plane, generated in a hollow space between opposite faces in the hollow space of permanent magnet constituents, wherein (A) shows a case of the present invention and (B) shows a case of a comparative example.

Measurement results on magnetic field distributions corresponding to the x-axis, y-axis, z-axis and a direction of 45° from the x-axis on an x-z plane generated in the hollow space between the opposite faces of the magnetic pole pieces in the configuration of the Embodiment 4 are shown in FIG. 12(A).

Comparative Example 4

Figure 9:
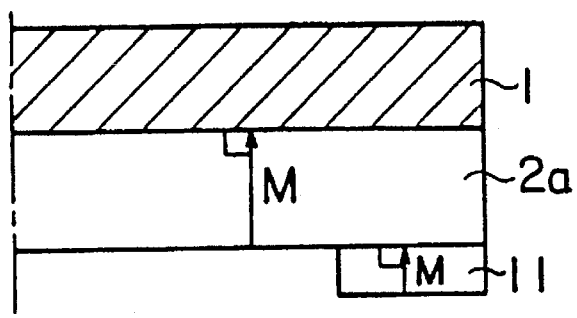
FIG. 9 is a schematic explanatory view showing a configuration of a permanent magnet shim of a conventional magnetic field generating apparatus for MRI.

A magnetic field generating apparatus of a comparison example, in which on both opposite end faces in the hollow space of the pair of permanent magnet constituents generating the main magnetic field, having the same configuration as the Embodiment 4 and whereon the magnetic pole piece and the projection consisting of the permanent magnet piece are not disposed, permanent magnet shims 11 as shown in FIG. 9 having the thickness of 70 mm, the width of 520 mm and the length of 205 mm in the z-axis direction, and having the same magnetizing direction as the permanent magnet constituent are disposed, is prepared.

Figure 12B:
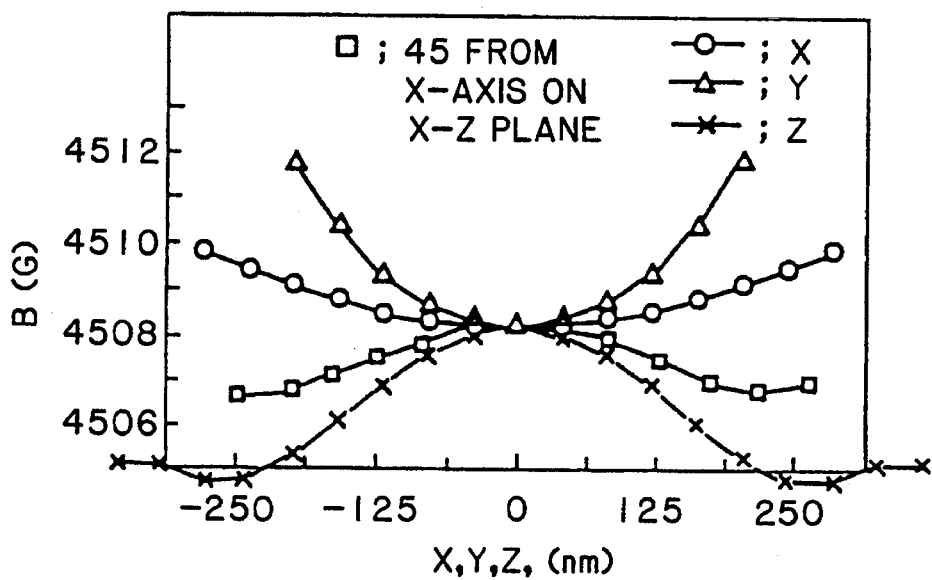

Measurement results of magnetic field distributions corresponding to the x-axis, y-axis, z-axis and a direction of 45° from the x-axis on the x-z plane, generated in the hollow space between the opposite faces in the hollow space of the magnetic pole pieces in the configuration of the Comparative Example are shown in FIG. 12 (B).

From FIG. 12, it is understood that, in the configuration of the Embodiment 4, as compared with the configuration of Comparative Example 4, the magnetic field distributions are uniformed throughout a wider range.

Embodiment 5

Figure 11:
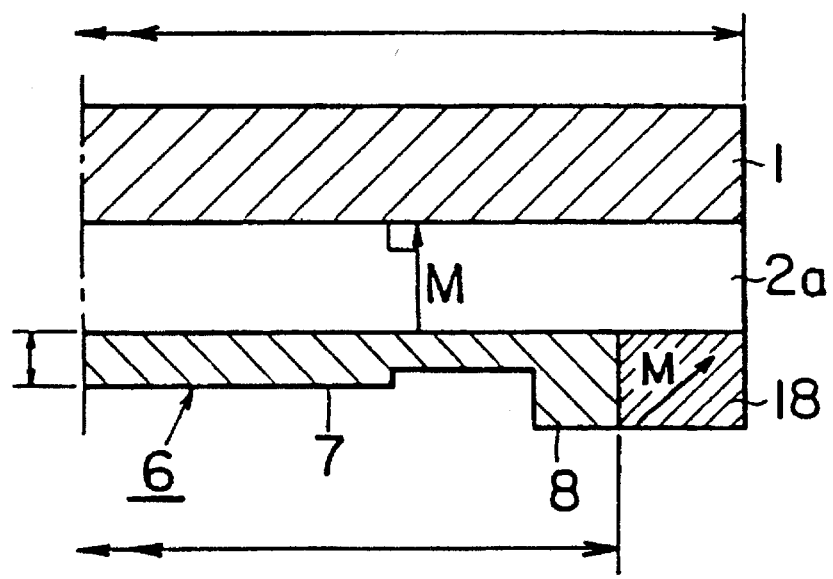
FIG. 11 is a schematic explanatory view showing a configuration of a magnet pole piece of a magnetic field generating apparatus for MRI according to the present invention.

In the configuration of the Embodiment 4 shown in FIG. 7 and FIG. 8 (A), though the magnetic pole pieces shorter than the length in the z-axis direction of the pair of permanent magnet constituents generating the main magnetic field, are disposed on the opposite faces in the hollow space of the permanent magnet constituents, as shown in FIG. 11, by disposing permanent magnet shims 18 having the magnetizing direction, which is inclined about 30° to 60° against the z-axis direction so as to open toward the opening portion of the magnetic circuit, on a bare magnet face where the magnetic pole piece is not disposed, formed on the both ends of the permanent magnet constituents, the magnetic field distributions can be improved and the weight of magnets can be reduced as compared with the conventional apparatus.

Embodiment 6

Figure 13:
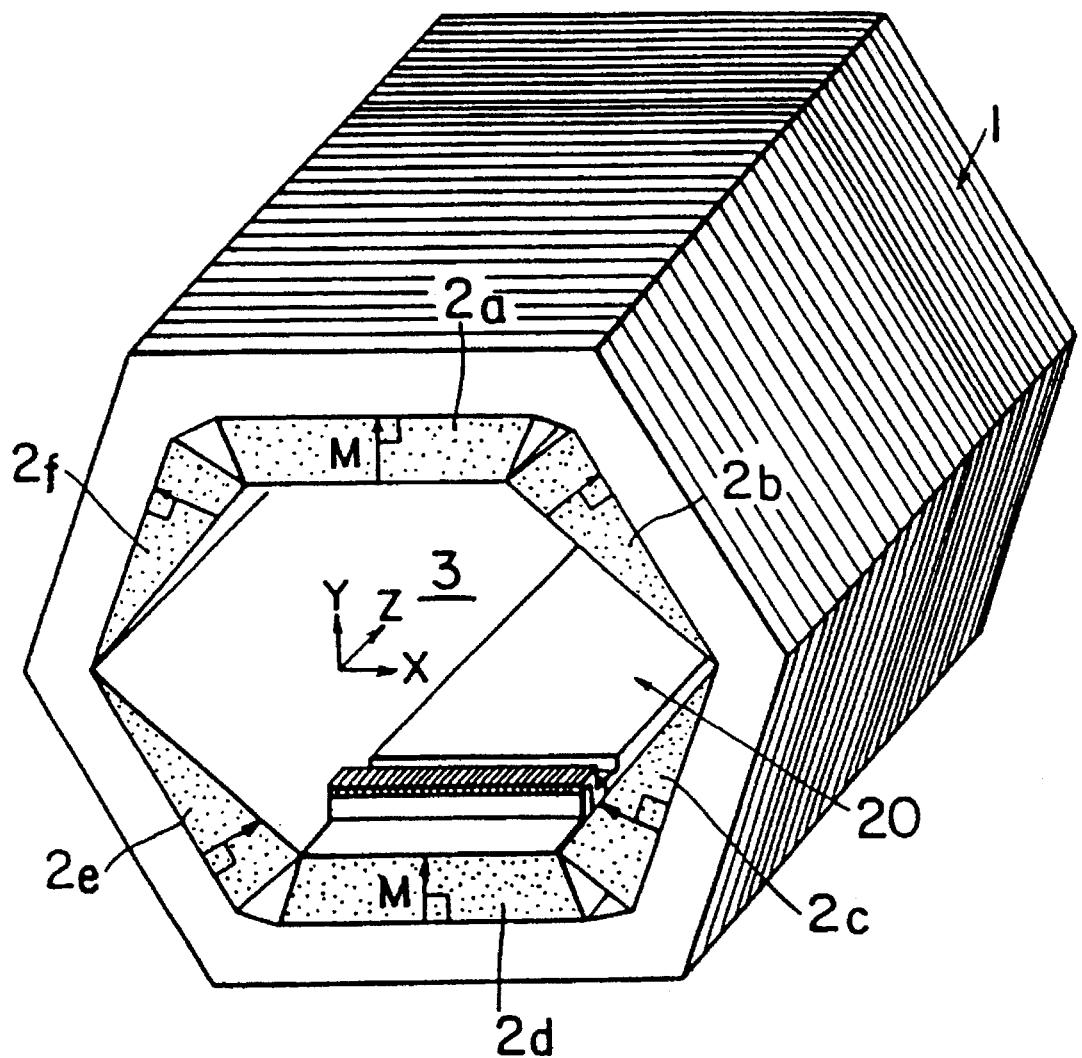
FIG. 13 is a perspective explanatory view showing an embodiment of a magnetic field generating apparatus for MRI in which the present invention is applied.

A magnetic field generating apparatus shown in FIG. 13 uses a hexagonal tubular yoke 1, consisting of laminates of silicon steel plates and the like, for reducing eddy currents, and is constituted such that permanent magnet constituents are disposed along its inner surface, a pair of permanent magnet constituents 2a, 2d serving as a main magnetic generating source contributing to formation of the magnetic field in a hollow space, usually, having the magnetizing direction in a magnetic field direction y-axis in the hollow space 3, and forming opposite faces therein.

Permanent magnet constituents designated by numerals 2b, 2c, 2e and 2f in the figure, where magnetic pole pieces are not disposed are constituted by a plurality of electrically insulated permanent magnet blocks so as to reduce the eddy currents generated in the permanent magnet constituents.

Figure 14A:
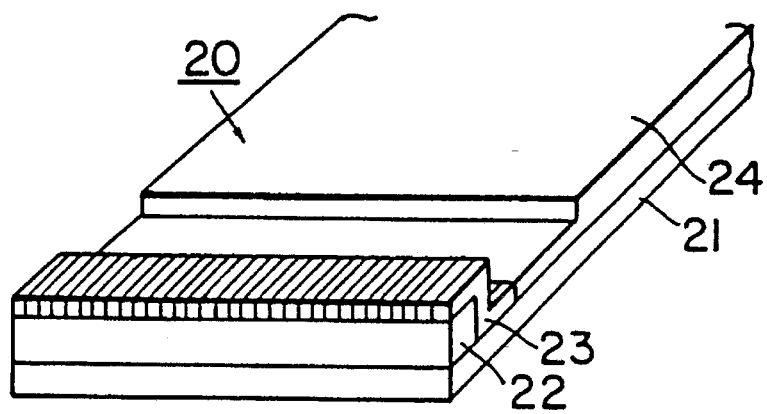
FIG. 14 (A), (B) and (C) are perspective explanatory views respectively showing the other configurations of magnetic pole pieces according to the present invention.
Figure 14B:
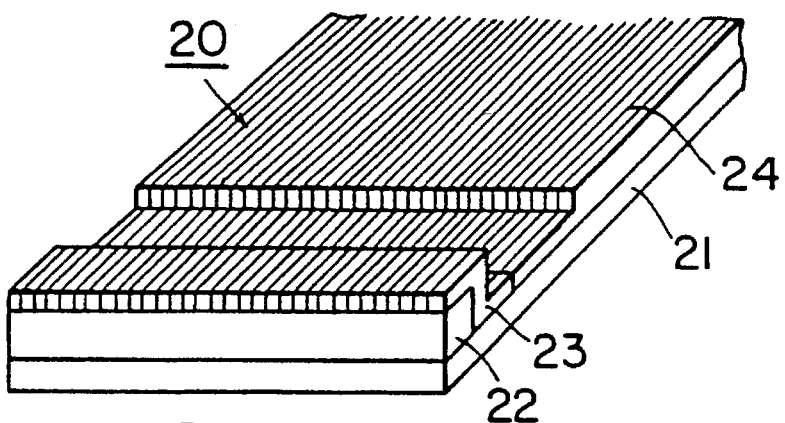
Figure 14C:
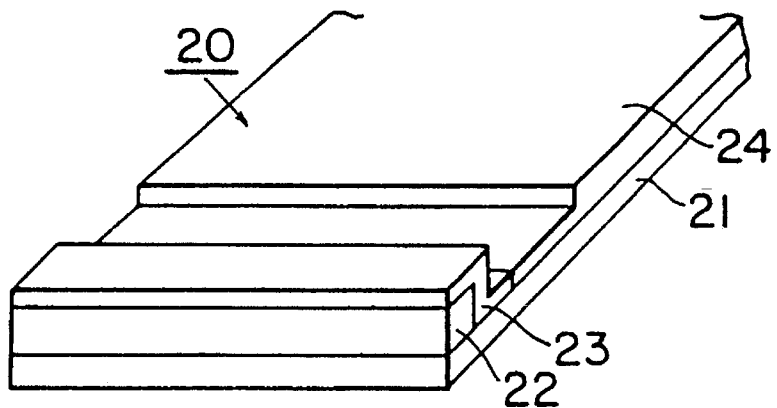
Figure 15:
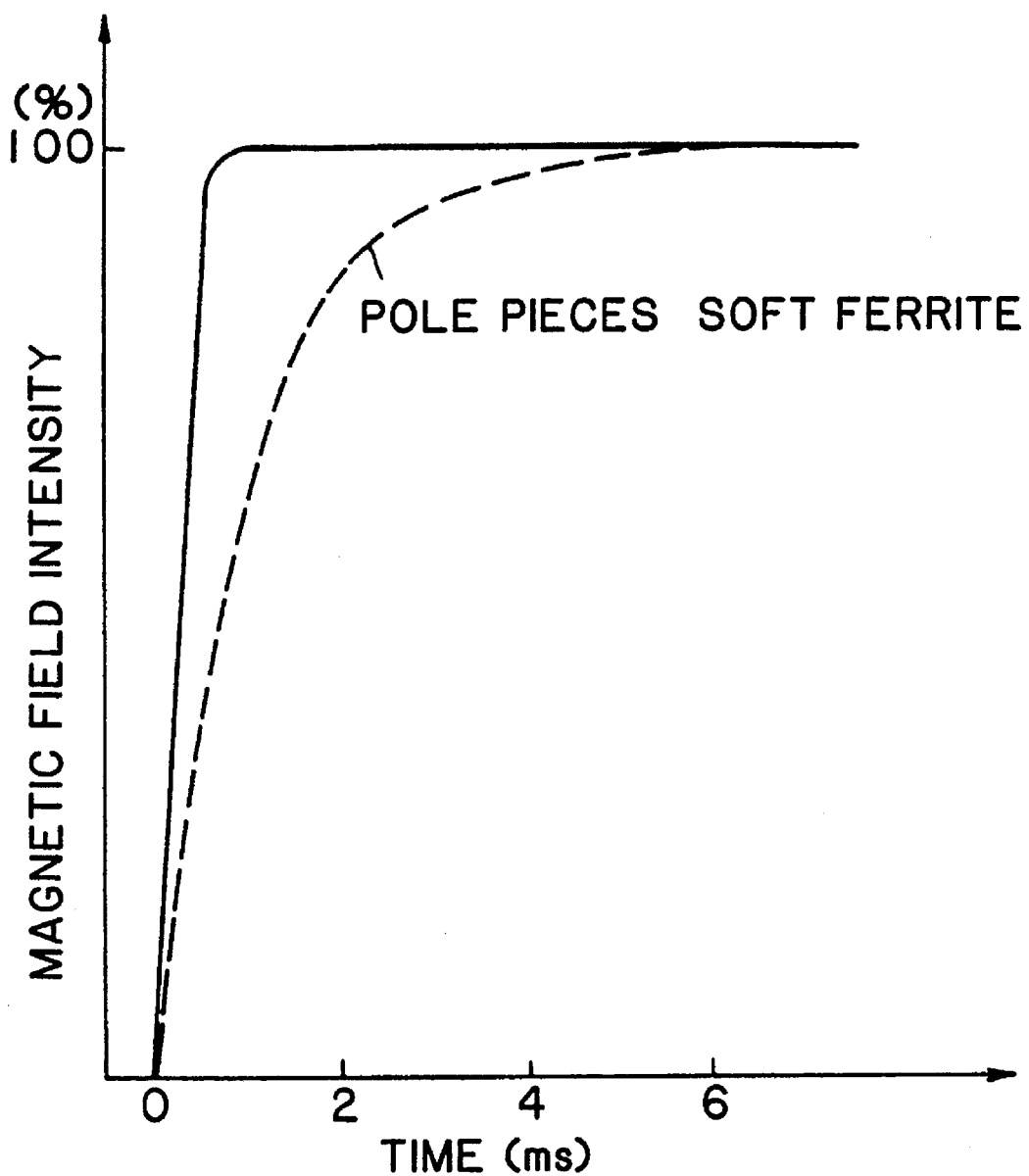
FIG. 15 is a graph showing the relationship between the time and gradient magnetic field intensity showing a building-up ratio of an gradient magnetic field.

As shown in FIG. 14 (A), magnetic pole pieces 20 are disposed on opposite faces in the hollow space of the pair of permanent magnet constituents forming the main magnetic field, and are fixed to the yoke 1 through the magnet by means of bolts and the like. As a material of its base 21, a soft magnetic material such as iron and the like can be selected suitably, shims 22 are disposed on both opposite face ends in the hollow space at the opening portions of the magnetic pole pieces 20. By forming the shims 22 and surface layers 23 in its vicinity by the silicon steel plate, the eddy currents generated in the vicinity of the projections at the both ends when applying GC pulses to gradient magnetic field coils are reduced.

Also, a center projection 24 is provided at the center of the magnetic pole pieces 20, and by forming the center projection 24 by a soft ferrite, the magnetic field in the hollow space is uniformed, thus it is effective in reducing the eddy currents caused by the gradient magnetic field coils, as well as, in reducing a residual magnetism produced by the GC pulses.

In the above-mentioned magnet field generating apparatus, since the silicon steel plate used in the both end projections of the magnetic pole pieces is constituted by laminating a plurality of electrically insulated sheets, in which a saturation induction Bs is high, the magnetic field uniformity in the hollow space is easy to achieve and a coercive force Hc and a hysteresis loss are small, even when the GC pulses are applied to the gradient magnetic field coils, the eddy currents generated in the vicinity of both end projections are reduced and the residual magnetism phenomenon can be reduced.

Also, by a soft ferrite layer of the magnetic pole piece surface layer, the magnetic field in the hollow space is uniformed, thus not only effective in reducing the eddy currents caused by the gradient magnetic field coils, but also effective in reducing the residual magnetism produced by the GC pulse, results in a clear tomographic image.

Besides the magnetic pole pieces 20 shown in FIG. 14 (A), the shims 22 of the magnetic pole pieces 20, its surface layer 23 and the center projection 24 may be constituted by the silicon steel plate laminates as shown in FIG. 14 (B), and the entire surface layer of the magnetic pole pieces 20 may be formed by the soft ferrite as shown in FIG. 14 (C).

The center projection 24 is provided at the center of the magnetic pole piece 20, and by forming the center projection 24 by the soft ferrite, the magnetic field in the hollow space is uniformed, thus it is effective in reducing the eddy currents caused by the gradient magnetic field coils, as well as, in reducing the residual magnetism produced by the pulse current.

In the above-mentioned magnetic field generating apparatus, since the silicon steel plate used in the both end projections of the magnetic pole pieces is constituted by laminating a plurality of electrically insulated sheets, in which a saturation induction Bs is high, the magnetic field uniformity in the hollow space is easy to achieve and a coercive force Hc and a hysteresis loss are small, even when the pulse current is applied to the gradient magnetic field coils, the eddy currents generated in the vicinity of both end projections are reduced and the residual magnetism phenomenon can be reduced.

Also, by a soft ferrite layer of the magnetic pole piece surface layer, the magnetic field in the hollow space is uniformed, thus not only effective in reducing the eddy currents caused by the inclined magnetic field coils, but also effective in reducing the residual magnetism produced by the pulse current, results in a clear tomographic image.

Besides the magnetic pole pieces 20 shown in FIG. 14 (A), the shims 22 of the magnetic pole pieces 20, its adjoining surface layer 23 and the center projection 24 may be constituted by the silicon steel plate laminates as shown in FIG. 14 (B), and the entire surface layer of the magnetic pole pieces 20 may be formed by the soft ferrite as shown in FIG. 14 (C). Though the example of providing the both end and center projections on the base material is shown, the configuration in which the both end and center projections consisting of the soft ferrite and silicon steel plate laminates may be provided directly on the permanent magnet constituents without the base material to form the magnetic pole pieces.

The permanent magnet constituents consisting of R-Fe-B type anisotropic magnets having BH max of 35 MGOe is used in the magnetic field generating apparatus having the same configuration of FIG. 13, and the magnetic pole pieces provided on opposite faces in the hollow space of the pair of permanent magnet constituents generating the main magnetic field are constituted such that, the projections are disposed on both ends of the pure iron base material, the projections and the adjoining surface layer are formed by the silicon steel plate, and the center projection made of soft ferrite is provided at the center.

In the configuration of the present invention, a distance between the opposite faces in the hollow space of the magnetic pole pieces is set to 500 mm, and a number of

17 pulsed gradient magnetic fields are added by applying the pulse current to the gradient magnetic fields coils, thereby to measure building-up characteristics of the gradient magnetic field and image characteristics. The non-oriented silicon steel plate is that, Hc=40A/m, Bs=1.7 T and $\rho$=45×10$^{-8}$ $\Omega$·m. The soft ferrite is a Mn-Zn ferrite, wherein Hc=6.0 A/m, Bs=0.58 T and $\rho$=0.2 $\Omega$·m. The pure iron is that, Hc=80 A/m, Bs=2.0 T and $\rho$=1×10$^{-7}$ $\Omega$·m.

Embodiment 7

For comparison, magnetic pole pieces entirely consisting of the pure iron having the above-mentioned properties and the same size and shape are disposed in the magnetic field generating apparatus of the Embodiment 6, and the gradient magnetic field buiding-up characteristics and the image characteristics are measured similarly.

The gradient magnetic field building-up characteristics of the magnetic field generating apparatus according to the present invention is that, against the case (shown by one-dot-cabin lines) of the magnetic field generating apparatus of the Embodiment 7 having the magnetic pole pieces consisting of pure iron, in the case of magnetic field generating apparatus of the Embodiment 6 (shown in solid lines), in which the projections are disposed on both ends of the pure iron base material, the projections and the adjoining surface layer are formed by the silicon steel plate, and the magnetic pole pieces having the center projection made of soft ferrite at the center thereof are provided, the gradient magnetic field building-up characteristics is considerably improved and a good image is obtained.

Embodiment 8

Figure 16:
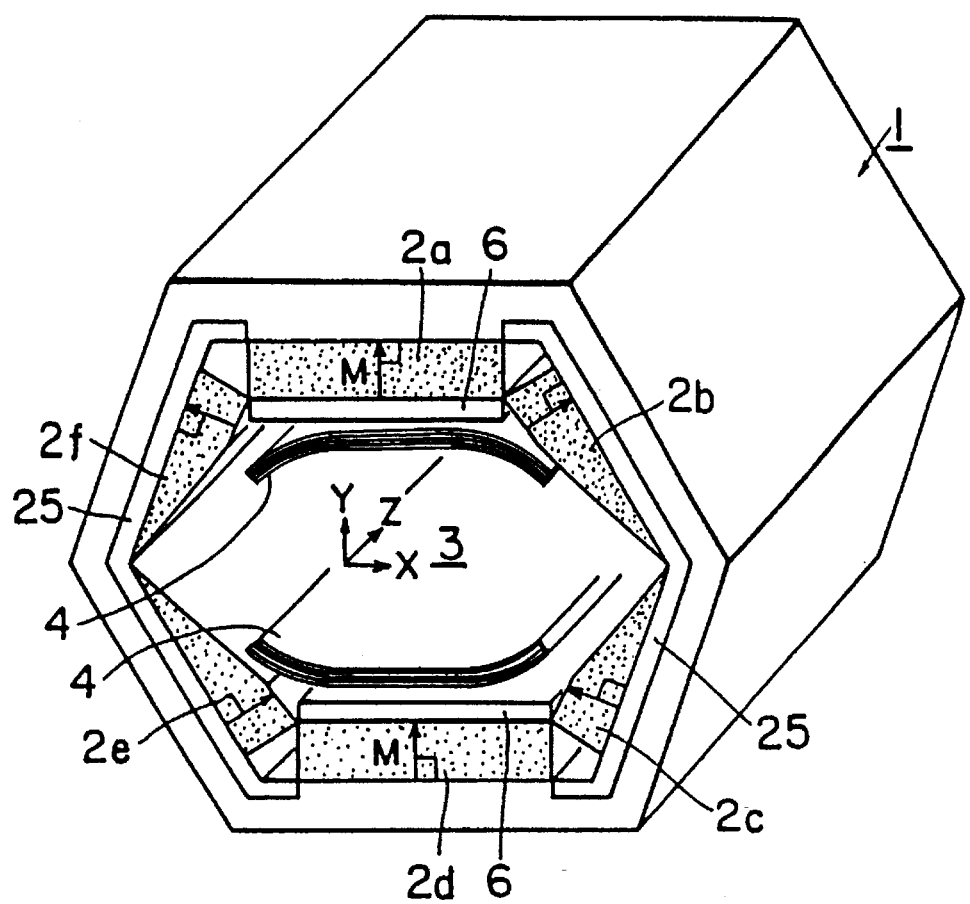
FIG. 16 is a perspective explanatory view showing an embodiment of a magnetic field generating apparatus for MRI according to the present invention.

In a magnetic field generating apparatus shown in FIG. 16, a hexagonal tubular yoke I consisting of bulk pure iron is used, a hollow space 3 is formed by disposing 6 types of permanent magnet constituents 2a to 2f angularly along the inner surface of the yoke 1, and gradient magnetic field coils 4 are disposed in the hollow space 3 to form a magnetic circuit therein.

Particularly described, in the figure, on upper and lower opposite faces in the hexagonal tubular yoke 1, sectionally rectangular permanent magnet constituents 2a, 2d having the magnetizing direction perpendicularly (vertically) are disposed, and on right and left opposite faces in the hexagonal tubular yoke 1, sectionally triangular permanent magnet constituents 2b, 2c, 2e and 2f having the magnetizing direction in the direction of allows are disposed, thereby the permanent magnet constituents 2a to 2f are disposed angularly along the inner surface of the yoke 1.

Respective permanent magnetic constituents are mainly constituted by a plurality of R-Fe-B type anisotropic magnet blocks having the size of 36 mm×40 mm×40 mm and a maximum energy product of 35 MGOe, which are electrically insulated from each other for integration.

On opposite faces of the pair of upper and lower permanent magnet constituents 2a, 2d, magnetic pole pieces 6, 6 consisting of the bulk pure iron, having projections at both ends of the opposite faces in the hollow space at opening portions and flat projections at the center are disposed, the surface layer of the bulk pure iron is consisting of soft ferrite.

Furthermore, on all inner faces of the yoke 1 except the faces whereon the pair of upper and lower permanent magnet constituents 2a, 2d are disposed, or on the right and left opposite faces, the sectionally triangular permanent

18 magnet constituents b, 2c, 2e and 2f are arranged by interposing silicon steel plate laminates 25, 25.

Figure 17:
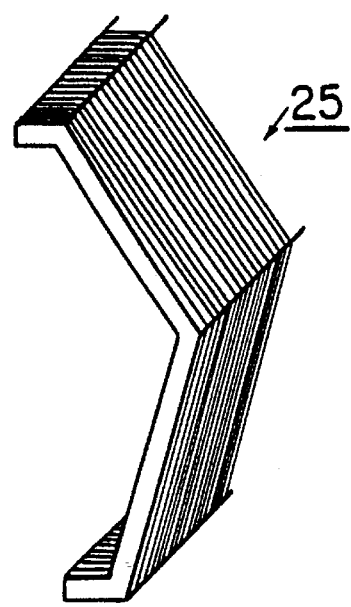
FIG. 17 is a perspective explanatory view showing a silicon laminate according to the present invention.
Figure 18:
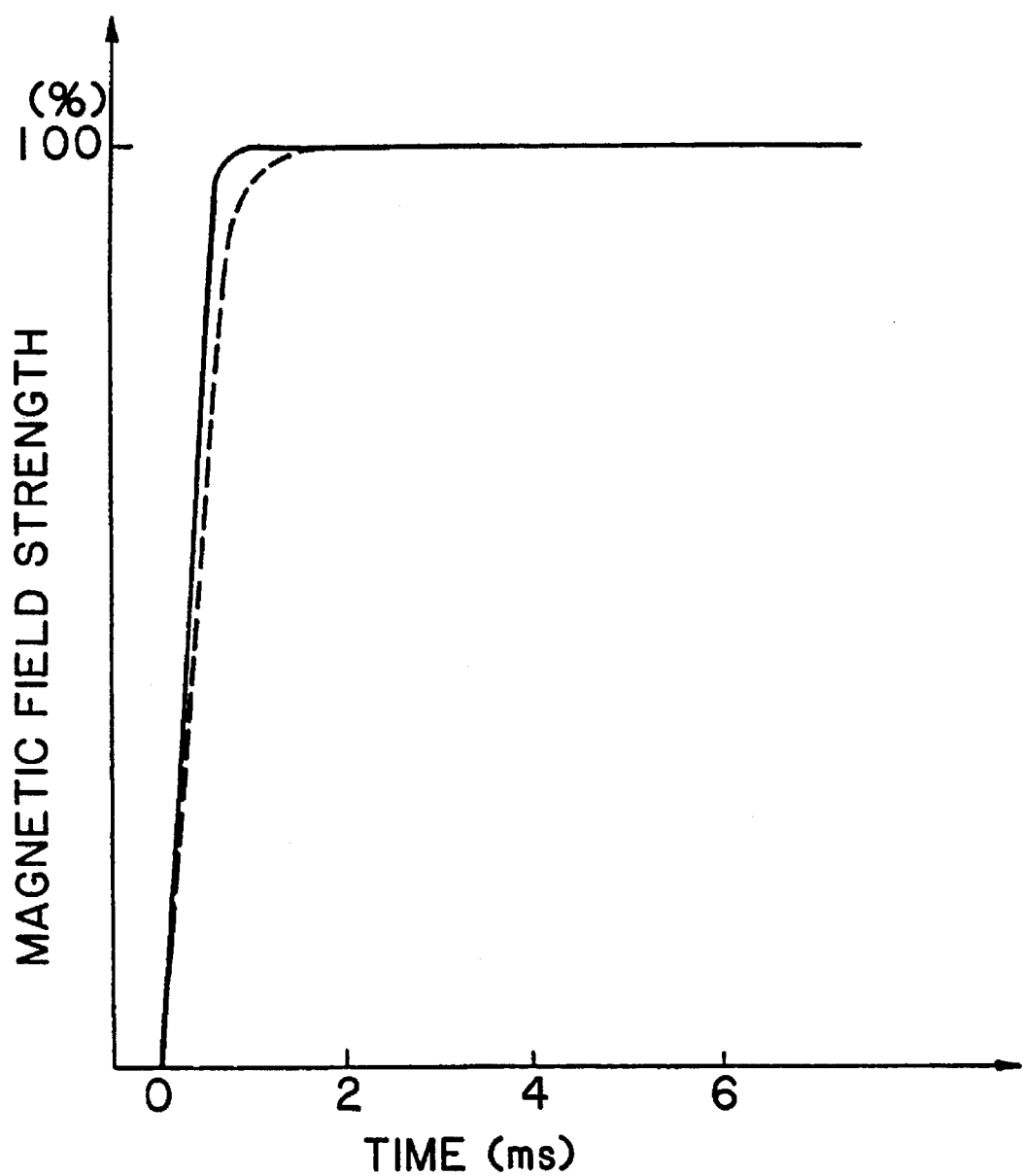
FIG. 18 is a graph showing the relationship between the time and gradient magnetic field strength showing a building-up ratio of an gradient magnetic field.

The silicon steel plate laminates 25, 25 are constituted by laminating the silicon steel plates, having a deformed C shape, in a direction of openings of the yoke 1 (direction z) as shown in FIG. 17.

The anisotropic silicon steel plate is that, Hc=40 A/m, Bs=1.7 T and $\rho$=45×10$^{-8}$ $\Omega$·m. The soft ferrite is Mn-Zn ferrite, and Hc=6.0 A/m, Bs=0.58 T and $\rho$=0.2 $\Omega$·m. The pure iron is that, Hc=80 A/m, Bs=2.0 T and $\rho$=1×10$^{-7}$ $\Omega$·m.

In the magnetic field generating apparatus according to the present invention having the above-mentioned configuration, a building-up ratio at the time of applying a pulse current to the gradient magnetic field coils is measured.

Embodiment 9

For comparison, the same building-up ratio of the gradient magnetic field is measured also in the magnetic field generating apparatus prepared at the same conditions, except providing the silicon steel plate laminate.

As shown in FIG. 16, the building-up characteristics of the gradient magnetic field of the magnetic field generating apparatus according to the present invention is improved in the case of magnetic field generating apparatus (shown by solid lines) of the Embodiment 8, having the silicon steel plate laminate on the disposed face of the permanent magnet constituents, against the case of magnetic field generating apparatus (shown by broken lines) of the Embodiment 9, having the hexagonal tubular yoke entirely consisting of pure iron.

INDUSTRIAL FIELD OF APPLICATION

The present invention is the, in a magnetic field generating apparatus for MRI constituted by, oppositely disposing a pair of permanent magnet constituents forming a main magnetic field, along the inner surface of a tubular yoke, and disposing permanent magnet constituents along the remaining inner surface of the yoke for electrical connection, the magnetizing direction of the all permanent magnet constituents is perpendicular to the contact face with the yoke, and gaps are formed at the adjoining portions of the permanent constituents, thereby the permanent magnet constituents can be assembled easily by permanent magnet blocks, a using efficiency of the magnets is improved and the apparatus can be miniaturized and lightened.

The present invention is that, by disposing magnetic pole pieces, which are shorter than the permanent magnet constituent in a z-axis direction on opposite faces in the hollow space of a pair of permanent magnet constituents generating the main magnetic field among the permanent magnet constituents, providing projections at both ends and center portion of the opposite faces in the hollow space of the magnetic pole pieces, and providing projections of the permanent magnet piece magnetized in the same direction as the permanent magnet constituents, on the opposite faces in the hollow space of both opening ends of the permanent magnet constituents whereon the magnetic pole piece is not disposed, magnetic field distributions can be uniformed throughout a wide range.

The present invention is that, by electrically insulating the magnet blocks of the permanent magnet constituents at right angles to its magnetizing direction for integration, eddy currents generated in the permanent magnets and the yoke can be reduced, and further, by using silicon steel plate laminates at desired positions of the yoke, as compared with the conventional apparatus using a bulk yoke, the eddy currents can be largely reduced.

The present invention is that, by constituting a main body of the magnetic pole piece by a magnetic material base such as soft iron, and by forming the surface layer of both end projections of the magnetic pole piece by laminated silicon steel plates or soft ferrite, or forming the surface layer other than the vicinity of the both end projections by the soft ferrite or silicon steel plate, generation of the eddy currents caused by the gradient magnetic field coils can be suppressed; particularly, since the silicon steel plate has a high saturation induction Bs, is easy to achieve the magnetic field uniformity of the hollow space, and is constituted by laminating a plurality of sheets having a small corrosive force Hc and hysteresis loss and electrically insulated, in the case of using the silicon steel plate in the surface layer of the both end projections, even when the pulse current is applied to the gradient magnetic field coils, the eddy currents generated in the vicinity of the both end projections are reduced, and a residual magnetism phenomenon can be reduced.

The present invention is that, by disposing the silicon steel plate laminates on the contact face with the yoke of the permanent magnet constituents whereon the magnetic pole piece is not provided, even when the pulse current is applied to the gradient magnetic field coils, the eddy currents generated in the yoke is reduced and the gradient magnetic field is built up rapidly, and further, since the silicon steel plate laminates are arranged effectively in the tubular yoke consisting of a bulk yoke, the entire tubular yake is not necessary to be made by the silicon steel plate and is easy to assemble, thus it is not only possible to provide at low cost, but also to improve the mechanical strength largely.

Thus, the present invention is that, a magnetic field generating apparatus for MRI, in which a stable and strong uniform magnetic field having a uniformity below $1 \times 10^{-4} \Omega \cdot m$ at 0.02 to 2.0 T, can be formed in an image-pick up visual field in the hollow space indispensable to the MRI, and eddy currents in the magnetic pole pieces caused by the gradient magnetic field coils and the residual magnetism phenomenon are reduced without spoiling the magnetic field uniformity in the hollow space, and further, a fast image pickup such as a FSE (Fast Spin Echo) method utilizing a pulse sequence, which switches the gradient magnetic field at high speed, is made possible, can be provided, or the magnetic field generating apparatus for MRI, in which a magnetic circuit can be assembled easily and the amount of permanent magnets being used is reduced to lighten the apparatus can be provided.

We claim:

1. A magnetic field generating apparatus for MRI, comprising:

a plurality of permanent magnet assemblies disposed continuously around the angular inner circumference of a hexagonal tubular yoke to provide a uniform magnetic field at a center portion of the hollow space formed inside said plurality of permanent magnet assemblies;

a pair of oppositely disposed permanent magnet assemblies forming a main magnetic field and having a trapezoidal or square cross-section;

other pairs of oppositely disposed permanent magnet assemblies having a triangular or substantially trapezoidal cross-section;

each of said pairs of oppositely disposed permanent magnet assemblies having a side surface in contact with a part of the inner peripheral surface of the yoke and forming a plurality of permanent magnet blocks which are magnetized perpendicularly to the side surface in contact with the yoke so that said permanent magnet assemblies are magnetized perpendicularly to the side surface thereof which is in contact with the yoke.

2. A magnetic field generating apparatus for MRI in accordance with claim 1, wherein resistivities of respective magnet blocks are below $10^{-3}$ $\Omega \cdot m$, and the respective permanent magnet blocks are electrically insulated from each other for integration.

3. A magnet field generating apparatus for MRI in accordance with claim 1, wherein respective permanent blocks are consisting of R-Fe-B type anisotropic permanent magnets.

4. A magnetic field generating apparatus for MRI in accordance with claim 1, wherein contact portions of a yoke with permanent magnet constituents are consisting of silicon steel plate laminates.

5. A magnetic field generating apparatus for MRI in accordance with claim 1, wherein gaps are formed between a pair of permanent magnet constituents forming a main magnetic field and the other permanent magnet constituents.

6. A magnetic field generating apparatus for MRI in accordance with claim 1, wherein an angle θ between opposite surfaces formed in the hollow space by the permanent magnet constituents, each having a triangular or substantially trapezoidal cross section, and an imaginary horizontal surface in the hollow spaces is in a range of from 45 to 90 degrees.

7. A magnetic field generating apparatus for MRI, comprising:

a plurality of permanent magnet assemblies disposed continuously around the angular inner circumference of a hexagonal tubular yoke to provide a uniform magnetic field at the center portion of the hollow space inside said permanent magnet assemblies;

said permanent magnet assemblies forming a main magnetic field by a pair of oppositely disposed permanent magnet assemblies which are trapezoidal or square in cross-section;

other pairs of permanent magnet assemblies having a triangular or square cross-section;

each of said pairs of oppositely disposed permanent magnet assemblies has a side surface in contact with a part of the inner peripheral surface of the yoke and forms a plurality of permanent magnet blocks which are magnetized perpendicularly to the side surface in contact with the yoke so that said permanent magnet assemblies are magnetized perpendicularly to the side surface thereof in contact with the yoke;

magnetic pole pieces disposed on each surface of the pair of oppositely disposed permanent magnet assemblies.

8. A magnetic field generating apparatus for MRI in accordance with claim 7, wherein gaps are formed between a pair of permanent magnet constituents forming a main magnetic field and the other permanent magnet constituents.

9. A magnetic field generating apparatus for MRI in accordance with claim 7, wherein said magnetic pole pieces include projections at both opposite face ends and/or at a center portion in the hollow space.

10. A magnetic field generating apparatus for MRI in accordance with claim 9, wherein said magnetic pole pieces are consisting of soft iron.

11. A magnetic field generating apparatus for MRI in accordance with claim 9, wherein said magnetic pole pieces are consisting of a silicon steel plate.

12. A magnetic field generating apparatus for MRI in accordance with claim 9, wherein said magnetic pole pieces are consisting of soft ferrite.

13. A magnetic field generating apparatus for MRI in accordance with claim 9, wherein said magnetic pole pieces are consisting of soft iron bases, projections disposed on both ends of the soft iron bases and soft ferrite or silicon steel plate portion having projections disposed at center portions of the soft iron bases.

14. A magnetic field generating apparatus for MRI in accordance with claim 13, herein projections disposed on both ends of the soft iron bases of said magnetic pole pieces are consisting of soft iron.

15. A magnetic field generating apparatus for MRI in accordance with claim 13, wherein at least, a surface layer of projections disposed on both ends of the soft iron bases of said magnetic pole pieces and its vicinity is consisting of laminated silicon steel plates.

16. A magnetic field generating apparatus for MRI in accordance with claim 13, wherein at least, a surface layer of projections disposed on both ends of the soft iron bases of said magnetic pole and its vicinity is consisting of soft ferrite.

17. A magnetic field generating apparatus for MRI in accordance with claim 7, wherein the length of said magnetic pole pieces in a z-axis direction (opening direction of a polygonal tubular yoke) is shorter than the length of a pair of permanent magnet constituents forming a main magnetic field in the z-axis direction.

18. A magnetic field generating apparatus for MRI in accordance with claim 17, wherein on both ends of a pair of permanent magnet constituents forming a main magnetic field, where the magnetic pole piece is not disposed, permanent magnet shims are disposed.

19. A magnetic field generating apparatus for MRI in accordance with claim 18, wherein the magnetizing direction of said permanent magnet shims is inclined by 30° to 60° against a z-axis direction so as to open toward on opening of a polygonal tubular yoke.

20. A magnetic field generating apparatus for MRI in accordance with claim 7, wherein contact portions of a yoke with permanent magnet constituents, where magnetic pole pieces are not disposed, are consisting of silicon steel plate laminates.

21. A magnet field generating apparatus for MRI, comprising:

a plurality of permanent magnet assemblies disposed continuously around the angular inner circumference of a hexagonal tubular yoke to provide a uniform magnetic field at the center portion of the hollow space inside said permanent magnet assemblies;

said permanent magnet assemblies forming a main magnetic field by a pair of oppositely disposed permanent magnet assemblies which are trapezoidal or square in cross-section;

other pairs of permanent magnet assemblies having a triangular or square cross-section;

each of said pairs of oppositely disposed permanent magnet assemblies has a side surface in contact with a part of the inner peripheral surface of the yoke and forms a plurality of permanent magnet blocks which are magnetized perpendicularly to the side surface in contact with the yoke so that said permanent magnet assemblies are magnetized perpendicularly to the side surface thereof in contact with the yoke;

magnetic pole pieces disposed on each surface of the pair of oppositely disposed permanent magnet assemblies;

and permanent magnet piece projections having the same magnetizing direction as said plurality of permanent magnet assemblies are respectively disposed on each surface of the paired oppositely disposed permanent magnet assemblies on which no magnetic pole piece is disposed.

22. A magnetic field generating apparatus for MRI in accordance with claim 21, wherein gaps are provided between a pair of permanent magnet constituents forming a main magnetic field and the other permanent magnet constituents.

23. A magnetic field generating apparatus for MRI in accordance with claim 21, wherein said magnetic pole pieces include projections at both opposite face ends in the hollow space and/or at a center portion.

24. A magnetic field generating apparatus for MRI in accordance with claim 21, wherein a polygonal tubular yoke assumes a hexagonal shape.

25. A magnetic field generating apparatus for MRI in accordance with claim 21, wherein a transverse cross section of a pair permanent magnet constituents forming a main magnetic field is a trapezoid or square shape, and a transverse cross section of the other permanent magnet constituents is a triangle or substantially trapezoid shape.

\* \* \* \* \*